United States Patent
Pierson et al.

(10) Patent No.: US 12,315,628 B2
(45) Date of Patent: May 27, 2025

(54) MEDICAL EQUIPMENT MANAGEMENT

(71) Applicant: ZOLL Medical Corporation, Chelmsford, MA (US)

(72) Inventors: John P. Pierson, Tewksbury, MA (US); Ian B. Durrant, Acton, MA (US); Kristopher M. Edgell, Shreveport, LA (US); Joanne R. Parrill, Andover, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 18/601,042

(22) Filed: Mar. 11, 2024

(65) Prior Publication Data

US 2024/0296942 A1   Sep. 5, 2024

Related U.S. Application Data

(63) Continuation of application No. 17/812,276, filed on Jul. 13, 2022, now Pat. No. 11,955,231, which is a
(Continued)

(51) Int. Cl.
*G16H 40/40* (2018.01)
*A61B 5/00* (2006.01)
(Continued)

(52) U.S. Cl.
CPC ............... *G16H 40/40* (2018.01); *G06F 8/65* (2013.01); *G06F 16/24573* (2019.01);
(Continued)

(58) Field of Classification Search
CPC ........ G16H 40/40; G16H 40/20; G16H 40/67; G06F 8/65; G06F 16/24573;
(Continued)

(56) References Cited

U.S. PATENT DOCUMENTS

| 6,747,556 B2 | 6/2004 | Medema et al. |
| 7,048,185 B2 | 5/2006 | Hart |

(Continued)

FOREIGN PATENT DOCUMENTS

| EP | 3236408 A1 | 10/2017 |
| JP | 2017-044480 A | 3/2017 |

(Continued)

OTHER PUBLICATIONS

US 8,639,774 B2, 01/2014, Gaines et al. (withdrawn)
Search Report and Written Opinion for PCT Application No. PCT/US2018/062731, dated Feb. 6, 2019. 30 pages.

*Primary Examiner* — Brandon J Miller
(74) *Attorney, Agent, or Firm* — Finch & Maloney PLLC

(57) ABSTRACT

A computer-implemented method for managing medical equipment includes presenting, at a display of a mobile computing device associated with an inspector, an inspection user interface configured to capture one or more user inputs from the inspector, receiving inspection account information via the one or more user inputs, receiving a location of the mobile computing device, providing, at the inspection user interface, identification information for transported medical equipment that is associated with the inspection account information, receiving status information for the transported medical equipment via the one or more user inputs, receiving, at a remote medical equipment database, location information for the transported medical equipment, and updating a maintenance report for the transported medical equipment by storing an inspection information entry in the maintenance report. The inspection information entry includes a time stamp, the location information, the received status information, and the location of the mobile computing device.

28 Claims, 12 Drawing Sheets

Related U.S. Application Data continuation of application No. 15/733,167, filed as application No. PCT/US2018/062731 on Nov. 28, 2018, now Pat. No. 11,424,024.

(60) Provisional application No. 62/594,645, filed on Dec. 5, 2017.

(51) Int. Cl.

| | | |
|---|---|---|
| *A61B 17/132* | (2006.01) | |
| *A61F 17/00* | (2006.01) | |
| *A61M 16/00* | (2006.01) | |
| *A61N 1/39* | (2006.01) | |
| *G01S 19/42* | (2010.01) | |
| *G06F 3/04847* | (2022.01) | |
| *G06F 8/65* | (2018.01) | |
| *G06F 16/2457* | (2019.01) | |
| *G06Q 10/087* | (2023.01) | |
| *G06Q 50/26* | (2024.01) | |
| *G16H 40/20* | (2018.01) | |
| *G16H 40/67* | (2018.01) | |
| *H04L 67/00* | (2022.01) | |
| *H04L 67/12* | (2022.01) | |
| *H04L 67/52* | (2022.01) | |
| *H04W 4/40* | (2018.01) | |
| *H04W 76/10* | (2018.01) | |

(52) U.S. Cl.
CPC ............ *G06Q 10/087* (2013.01); *G06Q 50/26* (2013.01); *G16H 40/20* (2018.01); *G16H 40/67* (2018.01); *H04L 67/12* (2013.01); *H04L 67/34* (2013.01); *H04L 67/52* (2022.05); *A61B 5/7475* (2013.01); *A61B 17/132* (2013.01); *A61F 17/00* (2013.01); *A61M 16/024* (2017.08); *A61N 1/3993* (2013.01); *G01S 19/42* (2013.01); *G06F 3/04847* (2013.01); *H04W 4/40* (2018.02); *H04W 76/10* (2018.02)

(58) Field of Classification Search
CPC .. G06F 3/04847; G06Q 10/087; G06Q 50/26; G06Q 10/20; H04L 67/12; H04L 67/34; H04L 67/52; A61B 5/7475; A61B 17/132; A61F 17/00; A61N 1/3993; G01S 19/42; H04W 4/40; H04W 76/10; H04W 4/029
See application file for complete search history.

(56) References Cited

U.S. PATENT DOCUMENTS

| | | |
|---|---|---|
| 7,510,526 B2 | 3/2009 | Merry et al. |
| 7,793,850 B1 | 9/2010 | Ho et al. |
| 8,095,403 B2 | 1/2012 | Price |
| 8,300,922 B1 | 10/2012 | Garvey, III |
| 8,319,632 B1 | 11/2012 | Vaisnys et al. |
| 8,526,910 B2 | 9/2013 | Messerly |
| 8,923,805 B2 | 12/2014 | Single |
| 8,996,393 B2 | 3/2015 | Sobie |
| 9,026,147 B2 | 5/2015 | Galvin et al. |
| 9,035,787 B2 | 5/2015 | Bongberg et al. |
| 9,220,912 B2 | 12/2015 | Elghazzawi |
| 9,301,132 B2 | 3/2016 | Ashley et al. |
| 9,324,120 B2 | 4/2016 | Braun |
| 9,482,739 B2 | 11/2016 | Mole et al. |
| 9,495,511 B2 | 11/2016 | Harrington et al. |
| 9,594,875 B2 | 3/2017 | Arrizza et al. |
| 9,619,767 B2* | 4/2017 | Braun ................ G06Q 50/265 |
| 9,703,931 B2 | 7/2017 | Hinkel |
| 9,769,610 B1 | 9/2017 | Gordon et al. |
| 9,928,478 B2 | 3/2018 | Ragusky et al. |
| 10,092,767 B1 | 10/2018 | Newton et al. |
| 11,424,024 B2* | 8/2022 | Pierson ................ H04L 67/52 |
| 11,955,231 B2* | 4/2024 | Pierson ................ H04L 67/12 |
| 2003/0069648 A1 | 4/2003 | Douglas et al. |
| 2003/0149759 A1 | 8/2003 | Hetherington et al. |
| 2006/0149322 A1 | 7/2006 | Merry et al. |
| 2007/0115137 A1 | 5/2007 | Lyon et al. |
| 2007/0174438 A9 | 7/2007 | Johnson et al. |
| 2008/0014869 A1 | 1/2008 | Demirbasa et al. |
| 2008/0250166 A1 | 10/2008 | Edwards |
| 2009/0099867 A1 | 4/2009 | Newman |
| 2010/0123547 A1 | 5/2010 | Stevenson et al. |
| 2011/0117878 A1 | 5/2011 | Barash et al. |
| 2012/0218102 A1 | 8/2012 | Bivens et al. |
| 2013/0040600 A1 | 2/2013 | Reitnour et al. |
| 2013/0087609 A1 | 4/2013 | Nichol et al. |
| 2013/0281818 A1 | 10/2013 | Vija et al. |
| 2013/0304147 A1* | 11/2013 | Aoyama ............ A61N 1/3937 455/66.1 |
| 2014/0002241 A1 | 1/2014 | Elghazzawi |
| 2014/0087762 A1 | 3/2014 | Galvin et al. |
| 2014/0236615 A1 | 8/2014 | Ragusky et al. |
| 2015/0163765 A1 | 6/2015 | Hobbs et al. |
| 2015/0173843 A1 | 6/2015 | Maughan et al. |
| 2015/0343227 A1* | 12/2015 | Elghazzawi ....... A61N 1/39044 607/5 |
| 2017/0003141 A1 | 1/2017 | Voeller et al. |
| 2017/0172424 A1 | 6/2017 | Eggers et al. |
| 2017/0173460 A1 | 6/2017 | Leu |
| 2017/0281461 A1 | 10/2017 | Kokubo et al. |
| 2018/0103343 A1 | 4/2018 | Vangipuram |
| 2021/0074417 A1 | 3/2021 | Pierson et al. |

FOREIGN PATENT DOCUMENTS

| | | |
|---|---|---|
| WO | 2007058835 A2 | 5/2007 |
| WO | 2007089225 A1 | 8/2007 |
| WO | 2009034506 A1 | 3/2009 |
| WO | 2009136259 A2 | 11/2009 |
| WO | 2013149982 A1 | 10/2013 |
| WO | 2016164368 A1 | 10/2016 |
| WO | 2017162627 A1 | 9/2017 |
| WO | 2017167708 A1 | 10/2017 |

* cited by examiner

MEDICAL EQUIPMENT MANAGEMENT

CROSS-REFERENCE TO RELATED APPLICATIONS

This is a continuation of U.S. patent application Ser. No. 17/812,276 (filed 13 Jul. 2022), which is a continuation of U.S. patent application Ser. No. 15/733,167 (filed 3 Jun. 2020, now U.S. Pat. No. 11,424,024), which was the National Stage of International Application PCT/US2018/062731 (filed 28 Nov. 2018), which claims the benefit of U.S. Provisional Patent Application No. 62/594,645 (filed 5 Dec. 2017). All subject matter set forth in the above referenced applications is hereby incorporated by reference in its entirety into the present application as if fully set forth herein.

BACKGROUND

Automated external defibrillators (AEDs) are generally made publicly accessible in order to reduce the response time to sudden cardiac arrest. Survival rates for victims of sudden cardiac arrest are typically reduced by ten percent for every minute of delay in providing resuscitative care. Therefore, timely defibrillation may be crucial for survival of the victims. As AEDs are used infrequently, routine inspections and maintenance may be necessary to ensure that AEDs are in working order. Similarly, routine inspections and maintenance of other types of medical equipment, including emergency equipment and non-publicly accessible equipment, may be necessary to ensure this equipment is in working order when needed for a response to a medical and/or emergency situation.

SUMMARY

An example of a computer-implemented method for managing medical equipment includes presenting, at an output device of a computing device, an user interface including an inspection user interface configured to capture one or more user inputs, receiving inspection account information via the one or more user inputs, receiving a location of the computing device, providing, at the output device, identification information for at least one item of medical equipment that is associated with the inspection account information, receiving status information for the at least one item of medical equipment, and updating previously stored status information for the at least one item of medical equipment with the received status information and the location of the computing device.

Implementation of such a computer-implemented method may include one or more of the following features. The method may include receiving the location of the computing device via the one or more user inputs. The method may include receiving a satellite positioning system based location of the computing device from a location module of the computing device. The method may include receiving an indoor location of the computing device from a location module of the computing device. The method may include receiving, from a remote server, the identification information for the at least one item of medical equipment, wherein the identification information is provided based on a predetermined inspection distance, evaluated at the remote server, between the computing device and the at least one item of medical equipment. The method may include identifying the at least one item of medical equipment based on a predetermined inspection distance, evaluated locally at the computing device, between the computing device and the at least one item of medical equipment and providing the identification information for the identified at least one item of medical equipment. The method may include obtaining a location of the at least one item of medical equipment. The method may include obtaining the location of the at least one item of medical equipment from a memory of the computing device. The method may include obtaining the location of the at least one item of medical equipment comprises receiving the location of the at least one item of medical equipment from a medical equipment database on a remote server. The method may include providing a user-interactive map on the user interface, receiving a user-input location for the at least one item of medical equipment, and storing the user-input location at one or more of the computing device and a remote database. The method may include obtaining the location of the at least one item of medical equipment comprises determining the location of the at least one item of medical equipment to be the location of the computing device. The predetermined inspection distance may be based on a physical distance between the computing device and the at least one item of medical equipment. The predetermined inspection distance may be a geographic area based on at least on part on the location of the at least one item of medical equipment. The predetermined inspection distance may be based on a transmission range for signals transmitted by the at least one item of medical equipment. The predetermined inspection distance may be based on an information capture range for one or more of a camera and an asset tag reader. The method may include selectively enabling user input of the status information for the at least one item of medical equipment based on a predetermined distance between the location of the computing device and a location of the at least one item of medical equipment. The method may include allowing capture of the status information if a distance between the location of the at least one item of medical equipment and the location of the computing device is within the predetermined distance and disallowing capture of the status information if the distance between the location of the at least one item of medical equipment and the location of the computing device exceeds the predetermined distance. The method may include providing the identification information as a list that includes a subset of the at least one item of medical equipment associated with the inspection account information and selectively enabling capture of status information for the subset of the at least one item of medical equipment included on the list. The method may include selecting the subset of the at least one item of medical equipment to include on the list based on a predetermined distance between the subset of the at least one item of medical equipment and the computing device. The method may include selecting medical equipment to include on the list based on the at least one item of medical equipment being located at one or more sites associated with the inspection account information. The one or more sites may be located within a predetermined distance from the computing device. The method may include sorting the one or more sites based on a distance between each of the one or more sites and the location of the computing device. The method may include receiving, via the one or more user inputs, a request for the list and providing the list in response to the request. The output device may be a display and the method may include providing the list as one or more of text information and mapping information. The mapping information may include one or more icons. The icons may indicate the location of one or more items of medical equipment. The method may include receiving the status information via the one or more user inputs. The method may include establishing a communicative coupling between the at least one item of medical equipment and the computing device. The communicative coupling may include one or more short-range communicative couplings. The short-range communicative coupling(s) may include at least one of near-field communications (NFC), Bluetooth® Low Energy, Zig-Bee®, and Bluetooth®. The method may include establishing the NFC is responsive to a proximity based interaction between the at least one item of medical equipment and the computing device. The proximity based interaction may include a tap-to-connect. The method may include pushing at least one of a software update and a configuration update from the computing device to the at least one item of medical equipment via the short-range communicative coupling. The method may include receiving the at least one of the software update and the configuration update from a server and storing the at least one of the software update and the configuration update at the computing device. The method may include streaming the at least one of the software update and the configuration update from a server to the at least one item of medical equipment via the computing device. The method may include providing at least one of a software update and a configuration update by the computing device to the at least one item of medical equipment via the short-range communicative coupling in response to a pull from the at least one item of medical equipment. The method may include receiving an inspection request at the computing device wherein the inspection request is pushed from the at least one item of medical equipment. The method may include transferring information between the computing device and the at least one item of medical equipment and providing, at the user interface, one or more of an indication that the information transfer is underway, a status report indicative of a progress of the information transfer, a distance beyond which the short-range communicative coupling will cease to support the information transfer, an indication that the information transfer is complete, and an error message that indicates that the information transfer is incomplete. The method may include establishing the communicative coupling comprises establishing the communicative coupling in response to receiving, at the computing device, a beacon signal from the at least one item of medical equipment. The method may include establishing the communicative coupling comprises establishing the communicative coupling via a communications device electronically coupled and peripheral to the at least one item of medical equipment. The method may include receiving the status information via the communicative coupling between the at least one item of medical equipment and the computing device. The status information may include inspection information. The status information may include one or more of battery information and electrode pad information. The method may include updating the previously stored status information comprises sending the status information to a remote database. Updating the previously stored status information may include saving the status information in a memory of the computing device. The at least one item of medical equipment may include one or more of public safety equipment, emergency equipment, and hospital equipment. The at least one item of medical equipment may include an external defibrillator.

An example of a non-transitory computer-readable storage medium storing a plurality of processor-executable instructions includes instructions that cause a processor to present, at an output device of a computing device, a user interface comprising an inspection user interface configured to capture one or more user inputs, receive inspection account information via the one or more user inputs, receive a location of the computing device, provide, at the output device, identification information for at least one item of medical equipment that is associated with the inspection account information, receive status information for the at least one item of medical equipment; and update previously stored status information for the at least one item of medical equipment with the received status information and the location of the computing device.

Implementations of such a non-transitory computer-readable storage medium may include one or more of the following features. The instructions may cause the processor to receive the location of the computing device via the one or more user inputs. The instructions may cause the processor to receive a satellite positioning system based location of the computing device from a location module of the computing device. The instructions may cause the processor to receive an indoor location of the computing device from a location module of the computing device. The instructions may cause the processor to receive, from a remote server, the identification information for the at least one item of medical equipment, wherein the identification information is provided based on a predetermined inspection distance, evaluated at the remote server, between the computing device and the at least one item of medical equipment. The instructions may cause the processor to identify the at least one item of medical equipment based on a predetermined inspection distance, evaluated locally at the computing device, between the computing device and the at least one item of medical equipment and provide the identification information for the identified at least one item of medical equipment. The instructions may cause the processor to obtain a location of the at least one item of medical equipment. The instructions may cause the processor to obtain the location of the at least one item of medical equipment from a memory of the computing device. The instructions may cause the processor to obtain the location of the at least one item of medical equipment comprise instructions that cause the processor to receive the location of the at least one item of medical equipment from a medical equipment database on a remote server. The instructions may cause the processor to provide a user-interactive map on the user interface, receive a user-input location for the at least one item of medical equipment, and store the user-input location at one or more of the computing device and a remote database. The instructions may cause the processor to obtain the location of the at least one item of medical equipment comprise instructions that cause the processor to determine the location of the at least one item of medical equipment to be the location of the computing device. The predetermined inspection distance may be based on a physical distance between the computing device and the at least one item of medical equipment. The predetermined inspection distance may be a geographic area based on at least on part on the location of the at least one item of medical equipment. The predetermined inspection distance may be based on a transmission range for signals transmitted by the at least one item of medical equipment. The predetermined inspection distance may be based on an information capture range for one or more of a camera and an asset tag reader. The instructions may cause the processor to selectively enable user input of the status information for the at least one item of medical equipment based on a predetermined distance between the location of the computing device and a location of the at least one item of medical equipment. The instructions may cause the processor to allow capture of the status information if a distance between the location of the at least one item of medical equipment and the location of the computing device is within the predetermined distance and disallow capture of the status information if the distance between the location of the at least one item of medical equipment and the location of the computing device exceeds the predetermined distance. The instructions may cause the processor to provide the identification information as a list that includes a subset of the at least one item of medical equipment associated with the inspection account information and selectively enable capture of status information for the subset of the at least one item of medical equipment included on the list. The instructions may cause the processor to select the subset of the at least one item of medical equipment to include on the list based on a predetermined distance between the subset of the at least one item of medical equipment and the computing device. The instructions may cause the processor to select medical equipment to include on the list based on the at least one item of medical equipment being located at one or more sites associated with the inspection account information. The one or more sites may be located within a predetermined distance from the computing device. The instructions may cause the processor to sort the one or more sites based on a distance between each of the one or more sites and the location of the computing device. The instructions may cause the processor to receive, via the one or more user inputs, a request for the list and provide the list in response to the request. The output device may be a display and wherein the instructions comprise instructions that cause the processor to provide the list as one or more of text information and mapping information. The mapping information may include one or more icons that indicate the location of one or more items of medical equipment. The instructions may cause the processor to receive the status information via the one or more user inputs. The instructions may cause the processor to comprising establishing a communicative coupling between the at least one item of medical equipment and the computing device. The communicative coupling may include one or more short-range communicative couplings. The short-range communicative coupling(s) may include at least one of near-field communications (NFC), Bluetooth® Low Energy, Zig-Bee®, and Bluetooth®. The instructions may cause the processor to establish the NFC responsive to a proximity based interaction between the at least one item of medical equipment and the computing device. The proximity based interaction may include a tap-to-connect. The instructions may cause the processor to push at least one of a software update and a configuration update from the computing device to the at least one item of medical equipment via the short-range communicative coupling. The instructions may cause the processor to receive the at least one of the software update and the configuration update from a server and store the at least one of the software update and the configuration update at the computing device. The instructions may cause the processor to stream the at least one of the software update and the configuration update from a server to the at least one item of medical equipment via the computing device. The instructions may cause the processor to provide at least one of a software update and a configuration update by the computing device to the at least one item of medical equipment via the short-range communicative coupling in response to a pull from the at least one item of medical equipment. The instructions may cause the processor to receive an inspection request at the computing device wherein the inspection request is pushed from the at least one item of medical equipment to the computing device. The instructions may cause the processor to transfer information between the computing device and the at least one item of medical equipment and provide, at the user interface, one or more of an indication that the information transfer is underway, a status report indicative of a progress of the information transfer, a distance beyond which the short-range communicative coupling will cease to support the information transfer, an indication that the information transfer is complete, and an error message that indicates that the information transfer is incomplete. The instructions may cause the processor to establishing the communicative coupling comprises establishing the communicative coupling in response to receiving, at the computing device, a beacon signal from the at least one item of medical equipment. The instructions may cause the processor to establish the communicative coupling comprises establishing the communicative coupling via a communications device electronically coupled and peripheral to the at least one item of medical equipment. The instructions may cause the processor to receive the status information via the communicative coupling between the at least one item of medical equipment and the computing device. The status information may include inspection information. The status information may include one or more of battery information and electrode pad information. The instructions may cause the processor to update the previously stored status information comprises sending the status information to a remote database. The instructions that may cause the processor save the status information in a memory of the computing device. The at least one item of medical equipment may include one or more of public safety equipment, emergency equipment, and hospital equipment. The at least one item of medical equipment may include an external defibrillator.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

DETAILED DESCRIPTION

Figure 1:
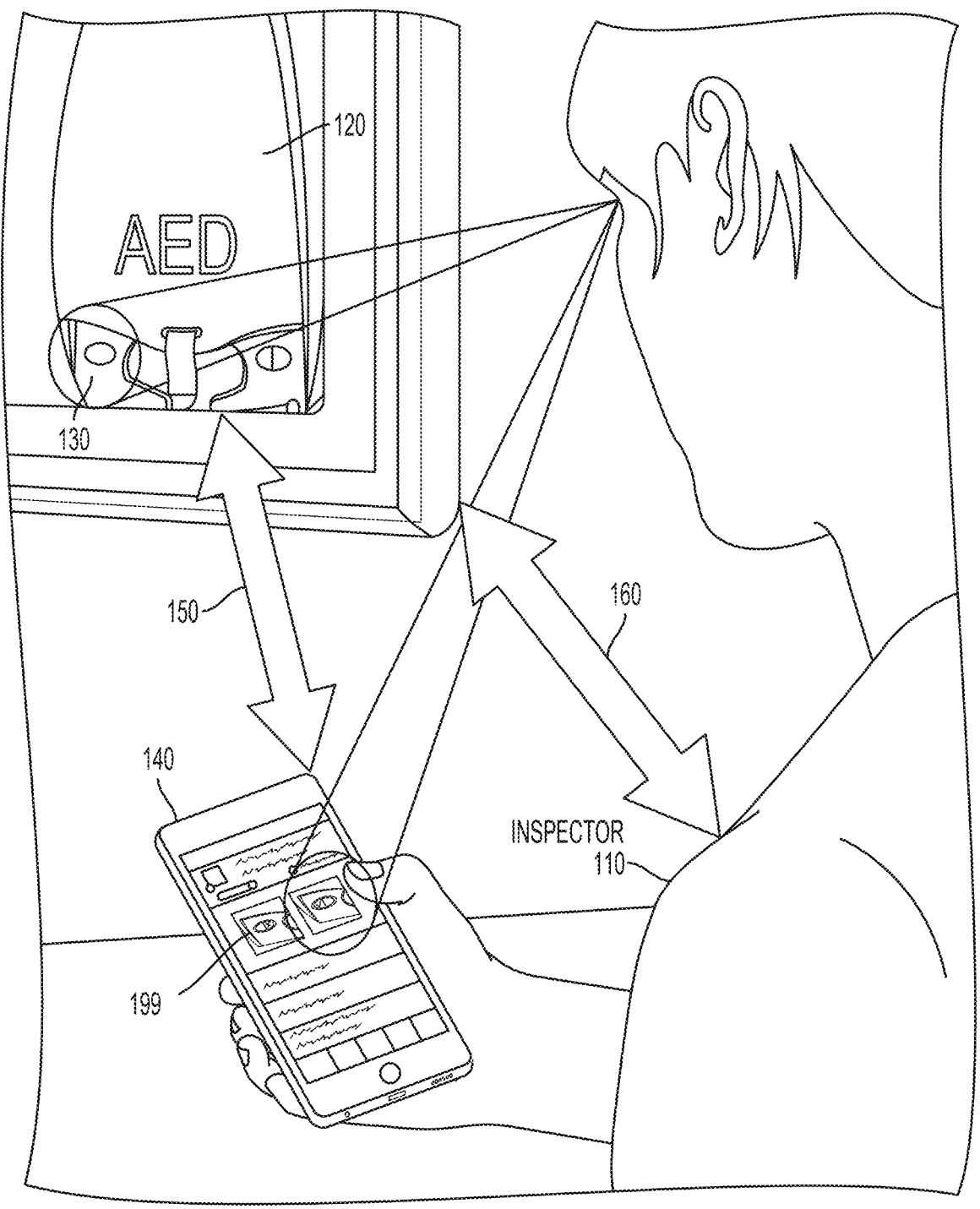
FIG. 1 shows an example of an inspection of medical equipment.

AEDs are typically publicly available and designed for ease of use without specialized training. In this way, a lay person, or a professional, may provide resuscitative care to a cardiac arrest victim within minutes of the cardiac arrest and possibly prior to treatment by medical professionals and/or emergency medical services. However, in order to ensure that the AEDs are ready for use and compliant with local regulations and/or manufacturer's guidelines, AEDs may require routine maintenance and inspection. In addition to publicly accessible AEDs, non-publicly accessible AEDs and other medical equipment (e.g., public safety equipment, emergency equipment, and/or hospital equipment) may require periodic inspections to ensure that this equipment is in working order at the time of use. For example, medical equipment that is subject to a maintenance cycle, has a life span or expiration date and/or includes parts with a life span or expiration date, and/or includes consumable parts may require periodic inspections. Examples include, but are not limited to, AEDs, external defibrillators, patient monitors, ventilation equipment, drug delivery equipment, physiological sensors, fire extinguishers, oxygen tanks, naloxone hydrochloride (e.g., Narcan®) kits, first aid kits, tourniquet equipment, etc. Techniques are presented herein to provide an equipment management system that tracks maintenance and inspection for medical equipment.

An owner, distributor, or other provider of medical equipment may purchase or otherwise secure access to a medical equipment management system. Such access may be via a medical equipment management system account. The medical equipment management system provides a medical equipment management software application, for example, via download from a computer network such as the Internet by a mobile device (e.g., a cellular phone, a smartphone, a tablet computer, etc.). This software application may be compatible with various mobile device operating systems (e.g., iOS, Android, etc.). The medical equipment management system tracks data captured by such a software application along with location information for the mobile device provisioned with the software application. In this way, the medical equipment management system may provide medical equipment management services and/or inspection tracking and verification. The medical equipment management services may include management and provision of software and/or configuration updates.

The medical equipment management software application may access a medical equipment database, for example, a medical equipment registry or a database listing of medical equipment owned by particular entities. The medical equipment database may include registered location information for equipment in the database. The registered location information may be provided by an owner, user, or administrator of the equipment and/or may be self-provided by the medical equipment via a communicative coupling between the medical equipment and the database.

An inspector of medical equipment may provide information related to the inspector's physical inspection of the medical equipment to the medical equipment management software application. For example, via the medical equipment management software application the inspector may select an AED and/or other medical equipment for inspection, provide a status of the AED and/or the other medical equipment, provide a status of AED components (e.g., battery, electrodes, etc.) and/or other medical equipment components, and/or order replacement parts for an inspected AED and/or an inspected item of other medical equipment. Additionally, the medical equipment management software application may enable the management and provision of software and/or configuration updates for the AED and/or the other medical equipment.

In an implementation, the inspector may determine the inspection information based on a visual inspection of the AED. The medical equipment management software application may use the location of the mobile device as the tracked location of the inspector. Based on the location information and the location of the mobile device, the software application may verify that the inspector is within a predetermined distance from the equipment. The predetermined distance may be a predetermined inspection distance. An indication of this verification may be stored in the database as a maintenance history for the equipment. In this manner, the software application and/or the database may provide a verified maintenance log for equipment inspections. In an implementation, the medical equipment and the mobile device may establish a short-range wireless communication channel. The short-range wireless communication channel may be responsive to a proximity-based interaction. The establishment of the short-range communication channel may provide a basis for a transfer and/or exchange of inspection information, software updates, and/or configuration updates between the mobile device and the medical equipment.

For a remote inspection of medical equipment, the medical equipment may self-report a status to a remotely located computing device. The remotely located computing device may generate a report for a remotely located inspector and/or an equipment administrator, user, and/or owner. The medical equipment may provide this report to the medical equipment management system.

Other capabilities may be provided and not every implementation according to the disclosure must provide all of the capabilities discussed. Further description and non-limiting illustrative examples of the medical equipment management software application are provided below.

Referring to FIG. 1, an example of an inspection of medical equipment 120 is shown. This example is described briefly here and in further detail below with regard to FIGS. 2A-10B. FIG. 1 shows an example of a physical inspection of the medical equipment 120 in which the inspector 110 and the mobile device 140 are proximate to the medical equipment 120, e.g., an AED. Because the mobile device 140 is in the hand of the inspector 110, the mobile device 140 is co-located with the inspector 110 (i.e., the distance 150 between the mobile device 140 and the medical equipment 120 is approximately equal to the distance 160 between the inspector 110 and the medical equipment 120). Therefore, the location of the inspector 110 relative to the medical equipment 120 may be determined from the location of the mobile device 140 relative to the medical equipment 120.

The distance between the mobile device 140 and the medical equipment 120 may be a predetermined distance such as a predetermined inspection distance. The predetermined inspection distance may be a separation between the mobile device 140 and the medical equipment 120 at which collection of inspection information is enabled and/or permitted by the medical equipment management software application on the mobile device 140. As discussed further below, the predetermined inspection distance may depend upon the manner in which the mobile device 140 and/or the inspector 110 obtain medical equipment status and/or inspection information.

In an implementation, the medical equipment 120 may include a status indicator 130. The mobile device 140 may provide visual replicas 199 of possible appearance of the status indicator 130. The possible appearance may include an appearance for "pass" and an appearance for "fail." The user 110 of the mobile device 140 may select the replica 199 that matches the status indicator 130 in order to record the inspection status of the medical equipment 120.

In an implementation, the distance between the mobile device 140 and the medical equipment 120 may correspond to a communications range. The communications range is a distance between the mobile device 140 and the medical equipment 120 that enables the mobile device 140 and the medical equipment 120 to communicate with one another via a short-range communications channel between these two entities. The distance may depend on a type of short range communication technology and/or protocol (e.g., near field communication (NFC), Bluetooth®, Bluetooth® Low Energy, Zig-Bee®, etc.). In an implementation, the existence of an established communications channel may determine that the mobile device 140 and the medical equipment 120 are sufficiently proximate for inspection and/or information exchange via the short-range communications channel. The information exchange may include an exchange and/or transfer of software and/or configuration updates between the mobile device 140 and the medical equipment 120. In an implementation, the communications range may include the pre-determined inspection distance.

Determining the location of the mobile device 140 relative to the medical equipment 120 at the time the inspector enters inspection information via the software application may enable detection and/or prevention of falsified inspection information by an inspector. For example, if the medical equipment management software application determines that the distance between the mobile device 140 and the medical equipment 120 exceeds the predetermined inspection distance, then the software application may generate and/or store an indication of false inspection information. This indication may be available to a management account manager. In this way, the software application may enable a detection by an account manager of fraudulent use of the inspection system by an inspector. Further, the software application may limit and/or disable the input of inspection information to the medical equipment management software application for one or more items of medical equipment 120 if the distance between the medical equipment 120 and the mobile device 140 exceeds the predetermined inspection distance. For example, the software application may only enable entry of inspection information for medical equipment 120 for a geographic area around the mobile device 140 location having a dimension (e.g., radius, diameter, side length, etc.) that approximately corresponds to the predetermined inspection distance. As another example, the software application may reject entry of inspection information for a particular item of medical equipment 120 if the distance between the mobile device 140 and the registered location of the medical equipment 120 exceeds the predetermined inspection distance.

Additionally, or alternatively, the predetermined distance may include a distance between the mobile device 140 and/or an area around the mobile device 140 in which the software application may accept medical equipment information other than inspection information. For example, authorization for entry of medical equipment information (e.g., registration information and/or other management account information) may be subject to geographic restrictions based on the location of the mobile device 140 (e.g., the mobile device 140 may be authorized for use for inspections in a particular country, city, facility, jurisdiction, business service area, etc.). As another example, emergency and/or medical treatment protocols, software updates, configuration updates, distributor management activities, etc. may vary based on geography and may require a particular location for the mobile device 140 coordinating these activities.

Figure 2A:
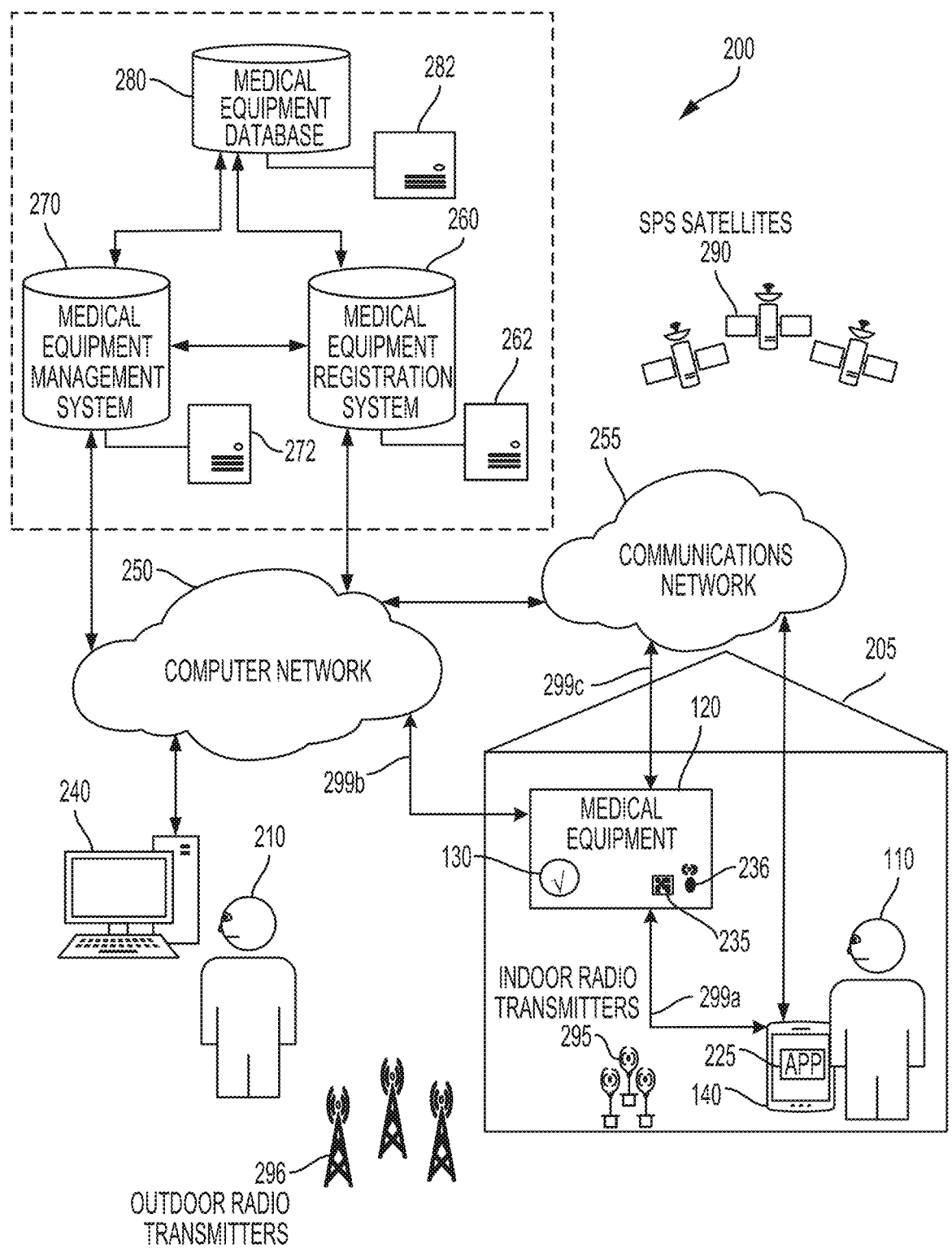
FIG. 2A shows a schematic diagram of an example of a system for medical equipment management and inspection tracking.

Referring to FIG. 2A, a schematic diagram of an example of a system for medical equipment management and inspection tracking is shown. A quantity of each component in FIG. 2A is an example only and other quantities of each, or any, component could be used.

Various entities in FIG. 2A are communicatively coupled via the computer network 250 and/or the communications network 255. The computer network 250 may include a mobile switching center and a packet data network (e.g., an Internet Protocol (IP) network referred to herein as the Internet). Although shown separately, the computer network 250 may be a portion of the communications network 255. The communications network 255 may include, but is not limited to, a wireless wide area network (WWAN), a wireless local area network (WLAN), a wireless personal area network (WPAN), and so on. A WWAN may be a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, and so on. A CDMA network may implement one or more radio access technologies (RATs) such as cdma2000, Wideband-CDMA (W-CDMA), Time Division Synchronous Code Division Multiple Access (TD-SCDMA), to name just a few radio technologies. A TDMA network may implement Global System for Mobile Communications (GSM), Digital Advanced Mobile Phone System (D-AMPS), or some other RAT. A WLAN may include an IEEE 802.11x network, and a WPAN may include a Bluetooth® network, an IEEE 802.15x, for example. Wireless communication networks may include so-called next generation technologies (e.g., "4G", "5G"), such as, for example, Long Term Evolution (LTE), Advanced LTE, WiMax, Ultra Mobile Broadband (UMB), and/or the like.

The system 200 includes a computing device 140, medical equipment 120, a medical equipment database 280, a medical equipment management system 270, and a medical equipment registration system 260.

The computing device 140 may be the mobile device (e.g., a cellular telephone) as depicted for example in FIG. 1. However, the cellular telephone is an example only and the computing device 140 may be any mobile computing device, including a tablet, a laptop, a wearable device, etc., and/or a personal computer, and/or a terminal for a server. In an implementation, the computing device 140 may be a group of communicatively coupled devices. Claimed subject matter is not limited to a particular type, category, size, etc. of computing device. Specific hardware components of the computing device 140 are discussed in detail with regard to FIG. 10A. These components include a processor 1010*a*, a memory 1020*a*, an input device 1030*a*, an output device

1040*a*, a location module 1050*a*, a transceiver 1070*a*, a camera 1080, a wired input/output port 1085*a*, and an asset tag reader 1090.

The medical equipment 120 in FIG. 2A may be an AED. However, this is an example only and the medical equipment 120 may include equipment other than AEDs such as public safety equipment, emergency equipment and/or hospital equipment, for example, but not limited to external defibrillators, patient monitors, ventilation equipment, drug delivery equipment, physiological sensors, fire extinguishers, oxygen tanks, Narcan® kits, first aid kits, tourniquet equipment, etc. The medical equipment 120 may include an asset tag (e.g., the barcode 235 and/or the radio frequency identification (RFID) tag 236) and/or a status indicator 130. The medical equipment 120 may further include one or more of the components shown in FIG. 10B and described in detail below in regard to FIG. 10B. These components include a processor 1010*b*, a memory 1020*b*, an input device 1030*b*, an output device 1040*b*, a location module 1050*b*, a transceiver 1070*b*, and a wired input/output port 1085*b*.

The database 280, the registration system 260, and the management system 270 are described below and shown in FIG. 2A as separate entities for clarity. However, one or more of these entities may be combined into a single entity. For example, the registration system 260 may be implemented as functions performed by the management system 270.

A user 210 may establish a management account with the management system 270 and a registration account with the registration system 260. In various implementations, the management account and the registration account may be separate accounts, may be combined as a single account, and/or may be linked accounts. One or more users 210 may have access to one or both of these accounts. The user 210 may include a user, manufacturer, inspector, owner, distributor, and/or other provider of the medical equipment. Although shown as separate entities in FIG. 2A, in an implementation, the user 210 may be the user 110 of the mobile device 140. The user 110 of the mobile device 140 may be an inspector. The user 210 may purchase a subscription or otherwise secure access to the management system 270. Such access may be via the management system account.

The registration system 260 may administer a website or other user accessible interface to capture the input of medical equipment information that may include medical equipment registration information. For example, the medical equipment registration information may be submitted by users 210 that are associated with a user account in the registration system 260 and/or in the management system 270. The registration system 260 may also capture the input of information regarding users and additional persons associated with the medical equipment, e.g. authorized users of the medical equipment, inspectors (for example, the inspector 110) associated with a user account, etc. The registration system 260 may store the captured information in the database 280.

In an implementation, a user 210 may access the registration system 260 via a remote computing device 240. The remote computing device 240 may be personal computer, a terminal interface for a server, or a mobile computing device such as, for example, a tablet, a laptop, a wearable device, or a cellular telephone. The remote computing device 240 may be a group of communicatively coupled devices. Claimed subject matter is not limited to a particular type, category, size, etc. of computing device. The remote computing device 240 may include a processor, a memory, an input device, an output device, and a computer network interface. The computer network interface may provide a wired and/or wireless connection between the remote computing device 240 and the computer network 250. The processor, memory, input device, and output device are substantially as described below with regard to the processor 1010*a*, the memory 1020*a*, the input device 1030*a*, and the output device 1040*a*.

The user 210 may establish a registration account with the registration system 260. The user 210 may provide the medical equipment registration information to the database 280 via the registration account. The registration account may be associated with registration login information and registration information. The registration login information may include, for example, but not limited to, a user name, a password, a security code, a hardware identification code, and/or a biometric input). The registration system 260 may store the medical equipment information in the database 280. Additionally, or alternatively, the registration system 260 may update previously stored information in the database 280 based on the registration information.

The database 280 may be a remote database that may be a centralized repository for medical equipment information including medical equipment registration information, medical equipment management information, and/or medical equipment inspection information. The medical equipment management information may include software and/or configuration update information and/or software and/or configuration updates. As discussed in further detail below, the database 280 and/or the medical equipment management system 270 may provide the software and/or configuration updates to the computing device 140 and/or the medical equipment 120 via the networks 250 and/or 255.

The medical equipment information may be associated, in the database 280, with a particular user, inspector, physical site, etc. The medical equipment information in the database 280 may include location information for the medical equipment, as well as information regarding specific users, user accounts, inspectors, physical sites, etc. associated with the medical equipment. As a result, the medical equipment information may be sortable based on one or more of user, inspector, physical site, etc. The medical equipment information may include information for public safety equipment, emergency equipment and/or hospital equipment. This equipment may include, for example, but not limited to, AEDs, external defibrillators, patient monitors, ventilation equipment, drug delivery equipment, physiological sensors, fire extinguishers, oxygen tanks, Narcan® kits, first aid kits, tourniquet equipment, etc.

The database 280 may service a geographic region such as a facility, a country, a state, a county, or a city. Additionally, or alternatively, the database 280 may service one or more private and/or public entities. For example, the entities may include dispatch centers, hospitals, volunteer organizations, businesses, community groups, etc.

For each item of medical equipment in the database 280, the database 280 includes medical equipment information, such as, but not limited to, one or more of an identifier of the item type (e.g., AED, patient monitor, external defibrillator, ventilation equipment, drug delivery equipment, physiological sensor, fire extinguisher, oxygen tank, Narcan® kit, first aid kit, tourniquet equipment, etc . . . ), a serial number, a manufacturer, a medical equipment status, inspection information, location information, contact information, medical equipment owner information, medical equipment manager information, a medical equipment usage log, training information, and registration account information.

The medical equipment inspection information may include the location of the computing device 140 at a time of inspection information entry, the time and/or date of inspection information entry, identification information for the inspected medical equipment, and/or an indication of whether the computing device 140 was within the predetermined inspection distance from the inspected medical equipment. The inspection information may further include status information for an item of medical equipment as a whole and/or status information for one or more components and/or accessories. For example, the status information for an AED may include battery information and/or electrode pad information. The status information may include expiration dates, inspection dates, order information, replacement information, and/or information on upcoming dates for replacement and/or inspections of components and/or accessories. The status information may include self-test and/or diagnostic results, such as a self-testing report uploaded to the database periodically after the medical equipment performs a self-test (either automatically or upon user initiation). The status information may additionally or alternatively include software update and/or configuration information. As other examples, the status information for a drug delivery device may include an expiration date for the drug, the status information for a fire extinguisher may include a pressure gauge reading, and the status information for a first aid kit may include a supply inventory and/or drug expiration dates.

The inspection information may additionally include a repair ticket and/or a replacement ticket. The repair ticket is a request for repair and the replacement ticket is a request for a replacement of one or more components and/or consumables for the inspected equipment. In an implementation, a medical equipment management software application 225 (e.g., as discussed in further detail below) and/or the management system 270 may automatically generate the repair ticket and/or the replacement ticket based on the received inspection information. The software application 225 may send the repair ticket and/or the replacement ticket to the medical equipment management system 270. The medical equipment management system 270 may notify an equipment administrator, owner, or service provider in order to implement the repair and/or replacement.

The contact information may enable the management system 270 and/or the registration system 260 to provide reminders and/or status updates to the one or more of the medical equipment owner, inspector, manager, distributor, user, and manufacturer. The contact information may include one or more of an email address, a mailing address, a web address, a telephone number, a text message enabled mobile telephone number, etc. The management system 270 and/or the registration system 260 may provide the reminders and/or status updates via one or more of email, physical mail, voice call, text message, website update, etc.

The medical equipment information in the database 280 may include location information. The location information may include a geolocation for the medical equipment determined based on a satellite positioning system (SPS). The geolocation may include a two-dimensional location in a global coordinate system (e.g., a latitude and longitude or other earth centered coordinates). The geolocation may further include an elevation (e.g., a three-dimensional location in a global coordinate system). The elevation may be a SPS-based elevation and/or may be an elevation determined based on an indicator of elevation such as barometric pressure. In an implementation, the location information may include indoor mapping information that includes indoor locations of medical equipment. In an implementation, and as discussed in further detail below, the database 280 may designate equipment as portable and the location stored in the database 280 may be editable and/or be able to be updated in conjunction with an inspection.

In an implementation, the registration system 260 may capture a user-input medical equipment location provided via the website for the registration system 260. For example, the user 210 may fill in a text field to provide the location information. The user-input medical equipment location may include a physical address of the medical equipment and/or a description of the physical location of the medical equipment. The physical address may include a street address. The registration system 260 may store the user-input medical equipment location in the database 280. In an implementation, the registration system 260 may convert the user-input medical equipment location to a geolocation. In an implementation the management system 270 may convert the user-input location for the medical equipment to an indoor location referenced to mapping information for the facility 205 in which the medical equipment is located.

In an implementation, the registration system 260 may capture the location of the medical equipment 120 via a mapping utility. For example, the registration system 260 may provide a map of an area that includes medical equipment via a mapping utility accessed by the registration system 260. In an implementation, the mapping utility may be a user interactive mapping utility. For example, the user may drag and drop a pin or other icon at a location on a displayed map that indicates the location of the medical equipment 120. The location of the pin may provide more accurate location information than the text field information described above. For example, the text field information may include a street address for a facility, like a hospital, that occupies and corresponds to a visible area on the map. The user may drag and drop the pin within the visible area to locate the medical equipment within the facility, for example, in a lobby of the hospital, in a parking lot, and/or in a treatment room. The mapping utility may convert the pin location to a geolocation and provide the geolocation to the registration system 260 for storage in the database 280. In an implementation, the medical equipment 120 may self-report a location to the registration system 260 based on the location information determined by the location module 1050b associated with the medical equipment 120.

The registration system 260, the management system 270 and the database 280 may be implemented as stored data and/or stored processor executable instructions in one or more non-transient memories of one or more servers 262, 272, and 282. One or more processors associated with the one or more servers 262, 272, and 282 execute these stored instructions and access the stored data to provide the functions of the registration system 260, the management system 270, and the database 280, as described above. The servers 262, 272, and 282 may be, for example, but not limited to, a network server, an enterprise server, a server associated with a particular website and/or application, a cloud network server, or a combination thereof. Although servers 262, 272, and 282 are shown in FIG. 2A as single servers for simplicity, other quantities of servers (e.g., one or more servers or a plurality of servers) could be used. The servers 262, 272, and 282 are computing devices including at least one processor and a memory and are configured to execute computer executable instructions. For example, the servers 262, 272, and 282 may be a computer system including a processor, non-transitory memory, a display, and a data input mechanism for a user. The processor may be an intelligent device, e.g., a personal computer central processing unit (CPU), a microcontroller, an application specific integrated circuit (ASIC), etc. The memory may include random access memory (RAM) and read-only memory (ROM). The memory includes a non-transitory processor-readable storage medium (or media) that stores processor-readable, processor-executable software code containing one or more instructions or code for controlling the processor to perform functions described herein. The software can be loaded onto the memory by being downloaded via a network connection, uploaded from a disk, etc. In an example, the servers 262, 272, and 282 are comprised of multiple server units. The multiple server units may be administered by one or more enterprises.

The management system 270 may provide and/or administrate a medical equipment management software application 225. The software application 225 may be a downloadable software application configured to operate on the computing device 140. In an implementation, the software application 225 may be downloadable or web-access software configured to operate on the remote computing device 240. The computing device 140 and/or the remote computing device 240 may download the software application 225 and/or access an associated website via a wired and/or wireless communicative coupling (e.g., a Wi-Fi®) and/or a cellular coupling) to a computer network 250 and/or a communications network 255. The software application 225 may be compatible with various mobile device operating systems (e.g., iOS, Android, etc.). The management system 270 may track data captured by the software application 225 and/or location information for the computing device 140 provisioned with the software application 225. In this way, the management system 270 may provide medical equipment management services and/or inspection tracking and verification services via the software application 225. In an implementation, the software application 225 may be web-access software accessible via the computer network 250. In an implementation, the software application 225 may enable and manage requests for and the provision of software and/or configuration updates for the medical equipment 120.

In an implementation, the medical equipment 120 may receive, send, and/or exchange information with the system 260 and/or 270 via communications with the computing device 140 and the software application 225 (e.g., as illustrated by the communications path 299a). Additionally or alternatively, the medical equipment 120 may receive, send, and/or exchange information with the system 260 and/or 270 via the computer network 250 and/or the communications network 255 (e.g., as illustrated by the communications paths 299b and 299c).

In an implementation, an equipment inspector (e.g., the inspector 110) and/or an equipment owner, administrator, coordinator, manufacturer, and/or distributor may establish an account with the management system 270. The software application 225 may enable access to the account.

The inspector 110 may be a user of the software application 225 with an established account. In an implementation, the inspector 110 may be associated with the equipment owner, administrator, coordinator, manufacturer, and/or distributor and/or may be associated with an agency and/or company that provides inspection services on behalf of the equipment owner, administrator, coordinator, manufacturer, and/or distributor. Alternatively or additionally, the inspector 110 may be a member of the general public and may operate the software application 225 to provide crowd-sourced inspection information. In this manner, any user of the software application 225 may provide the management system 270 and/or the database 280 with inspection information. In an implementation, the management system 270 and/or the database 280 may associate each registered user of the software application 225 with identification information that indicates whether the registered user is an officially sanctioned inspector or a crowd-source inspector. In response to a crowd-sourced inspection report indicating that an item of medical equipment 120 does or does not satisfy a "pass" status, the system 270 may notify an officially sanctioned inspector to re-visit the item of medical equipment and verify the crowd-sourced inspection report.

The account may be an inspection account and/or a management account. The inspection account may be a separate account from the management account for a set of medical equipment but may be linked to the management account. Alternatively, the inspection account and the management account may be the same account (e.g., a combined account). The inspection account may provide inspection access privileges and the management account may provide management access privileges. The combined account may provide inspection or management access privileges based on the user being an inspector or manager, as identified by the login information. Inspection access privileges may differ from management access privileges. For example, the management access privileges may allow a medical equipment owner, a medical equipment coordinator for a site, a medical equipment distributor and/or manufacturer, and/or other medical equipment managers to add medical equipment or other information to the database 280 and/or otherwise edit the database 280, manage software and configuration updates, receive reports and/or other notifications for medical equipment owned and/or coordinated by an entity, and/or view, edit, or add inspection information, consumable information, repair and/or replacement information. In contrast, the inspection access privileges may allow an inspector to log inspections and view, add, and/or edit requests for parts and/or repair. However, the inspection access privileges may exclude the ability to edit the database 280, add and/or delete medical equipment or other information to and/or from the database 280, to manage software and configuration updates, and/or to receive reports and/or other notifications for medical equipment owned and/or coordinated by an entity.

A user of the software application 225 may obtain login information for the software application 225. The login information may include, for example, but not limited to, a user name, a password, a security code, a hardware identification code, and/or a biometric input. For example, the login information for the software application 225 may include account information for one or more management system accounts and/or account information for one or more inspection accounts. The login information and/or the associated account information may identify the user as an inspector or as a manager or as both.

Each management system account and/or inspection account may include information for one or more items of medical equipment registered in the database 280. Therefore, based on the login information and/or the account information, the user of the software application 225 may have access to the medical equipment information stored in the database 280 for medical equipment associated with the one or more management system accounts and/or the one or more inspection accounts. The software application 225 may display, or otherwise make available to the user, the medical equipment information associated with the one or more management system accounts and/or the one or more inspection accounts.

Figure 3:
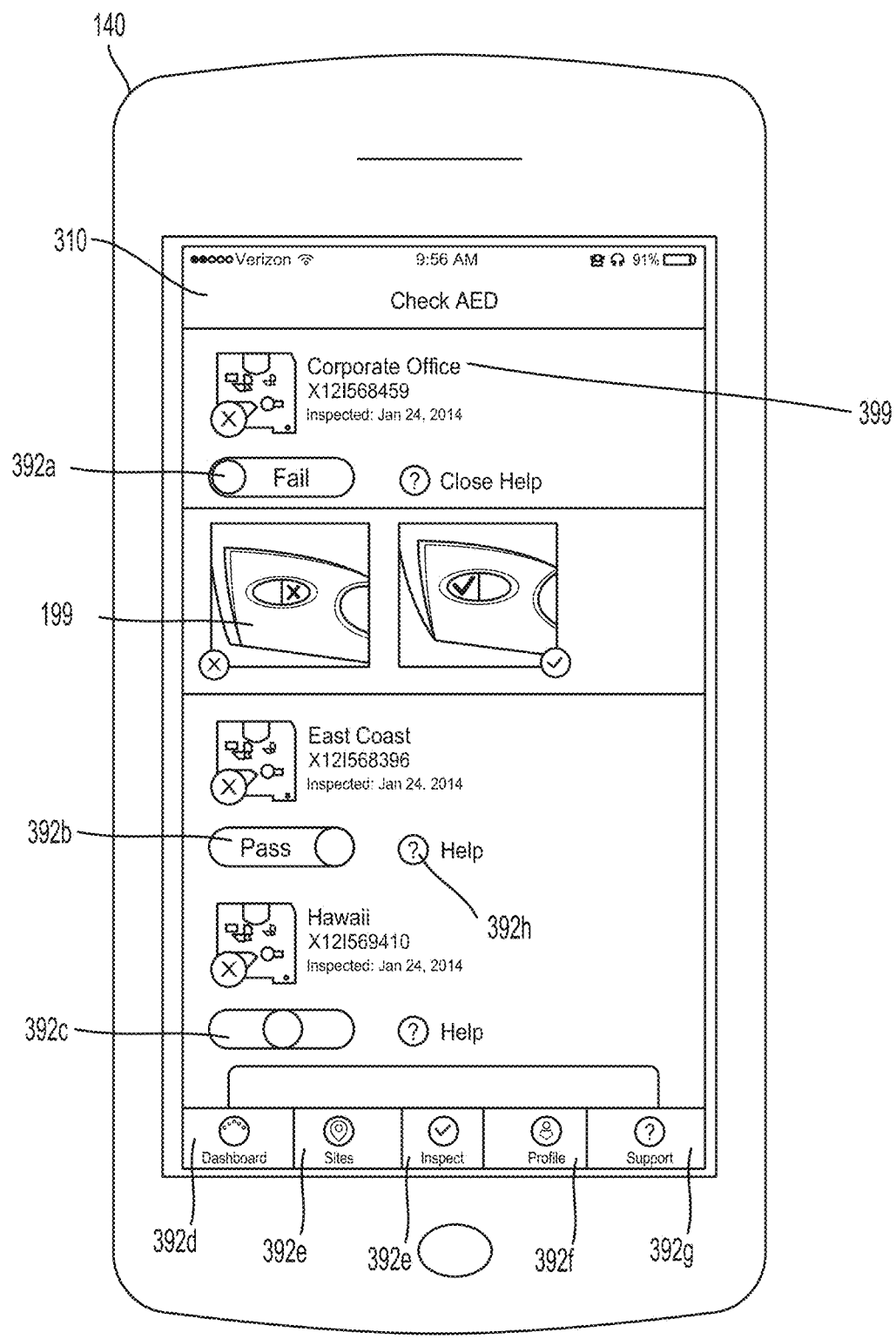
FIG. 3 shows an example of an inspection user interface.
Figure 5:
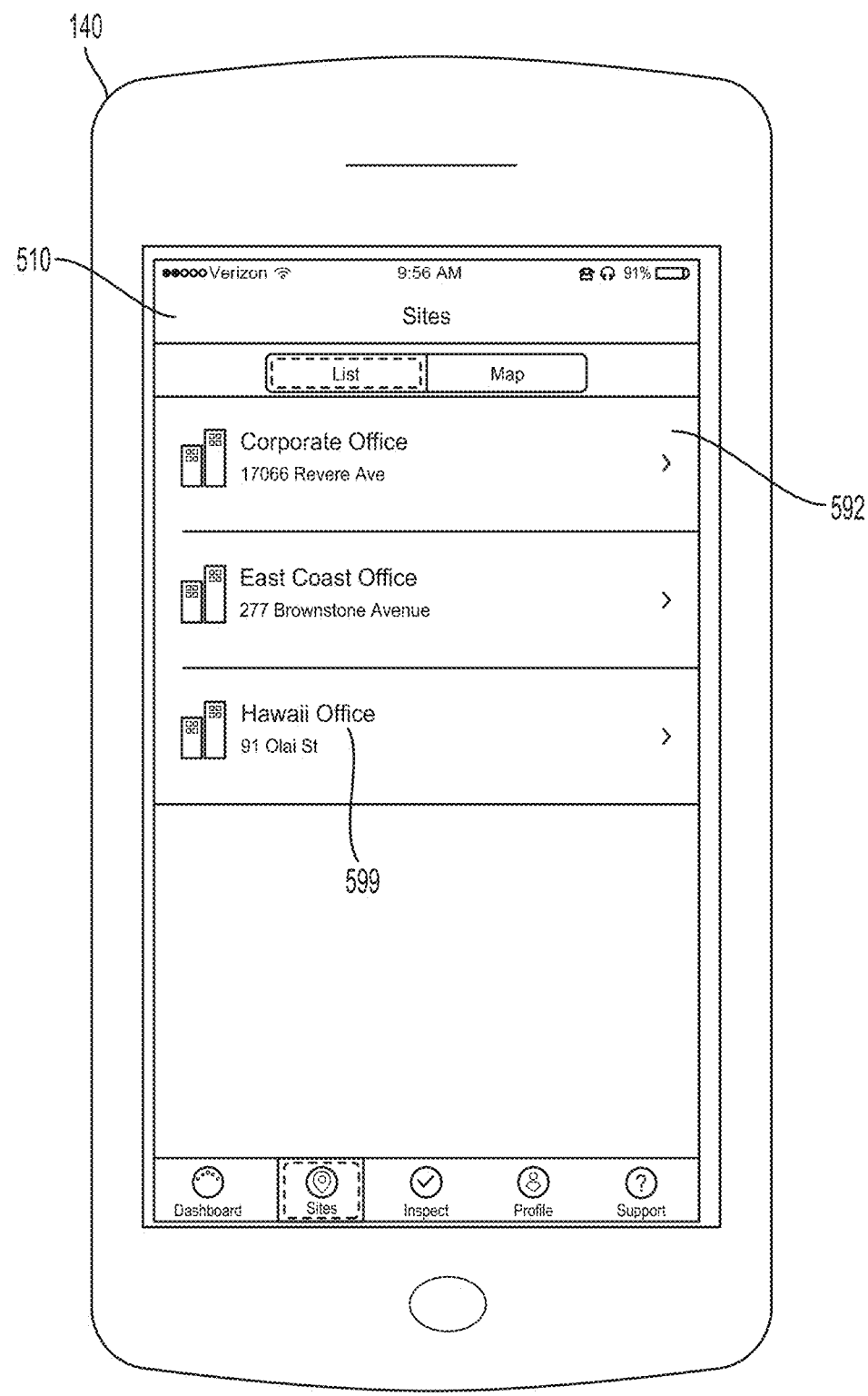
FIG. 5 shows an example of a text list for a medical equipment management software application.
Figure 6:
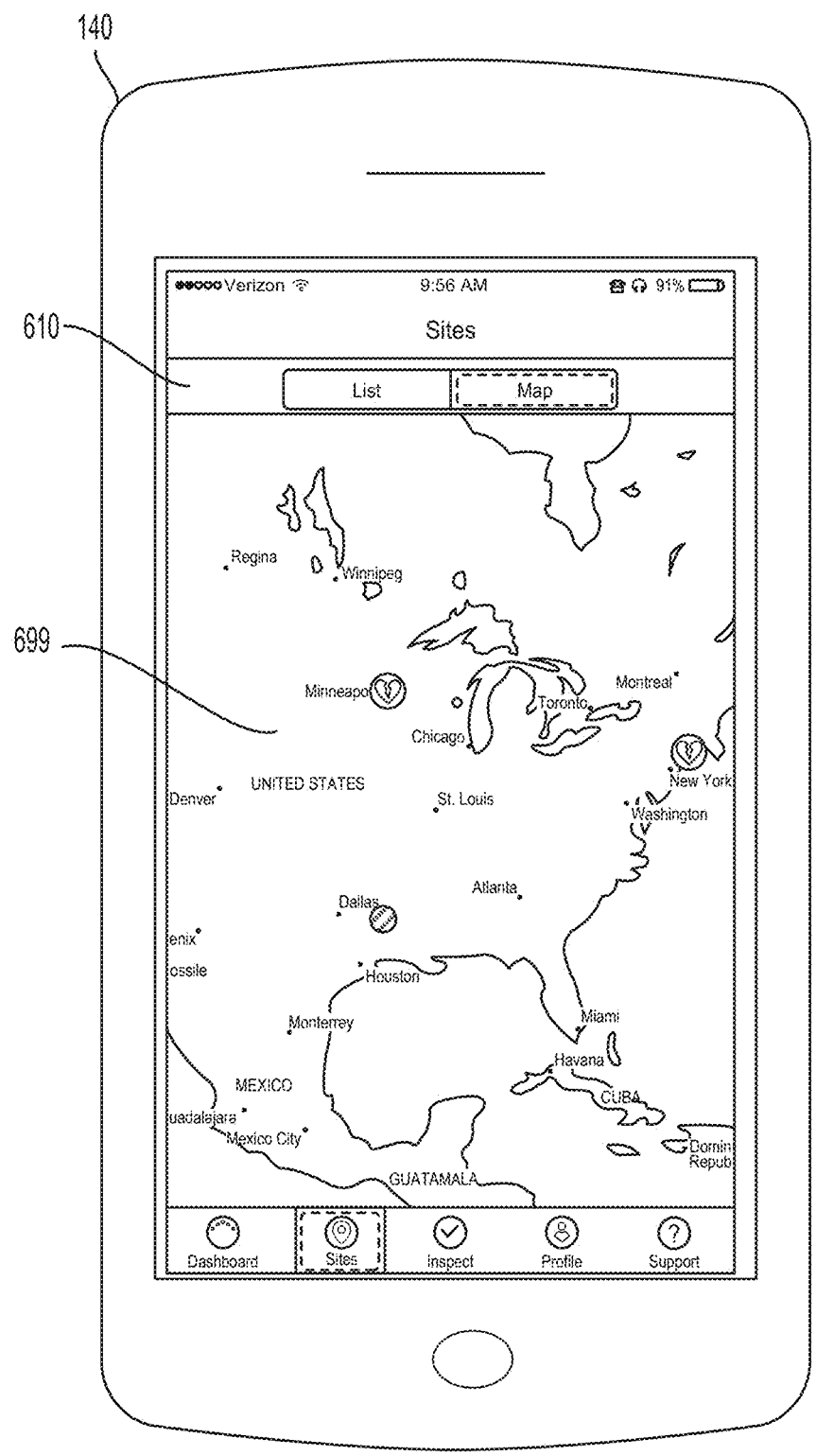
FIGS. 6 and 7 show examples of mapping information for a medical equipment management software application.

Referring to FIG. 3, the software application 225 may include a user interface, for example, the inspection user interface 310. Via the inspection user interface, the software application 225 may capture inspection information that is input to the user interface for the medical equipment. The inspection user interface 310 is an example of an inspection information entry screen. For example, the inspection user interface 310 may include multiple user inputs, e.g., 392a, 392b, 392c, 392d, 392e, 392f, 392g, and 392h. In this example, the user inputs 392a-392c enable input of inspection information that is received by the software application 225. The user inputs 392d-392h enable input of user selections of various functions of the software application 225. Referring briefly to FIGS. 5 and 6, the software application 225 may also include user interfaces 510 and 610 that provide user inputs (e.g., the user selection option 592) to select medical equipment. For example, via the inspection user interface 510 of the software application 225, the inspector may select medical equipment for inspection (e.g., the inspector may select the AED in the Corporate Office) with the user selection option 592. The user interfaces 310, 510, and 610 show examples of identification information for the medical equipment. On interfaces 310 and 510, this is shown as text information 399 and 599 respectively. On the interface 610, this is shown as mapping information (e.g., the low-resolution map 699). An example of identification information is also found in FIG. 7, namely the identification information 720. On the user interface 310, the user may provide a status of the selected medical equipment and/or components thereof via the user input 392a (e.g., battery, electrodes, drugs, etc.), and/or order replacement parts or repairs. For example, as shown in FIG. 3, the AED in the Entrance Foyer has a "fail" status for the inspection and the AED on the East Coast as a "pass" status of the inspection. Further, the date of the inspection is shown. Although the inspection user interface 310 as shown in FIG. 3 refers to AEDs, this interface may refer to other types and/or multiple types of medical equipment such as, for example, but not limited to public safety equipment, emergency equipment and/or hospital equipment. In an implementation, the software application 225 may be configured to receive the location information and/or the identification information for the medical equipment 120 via the input device 1030a. The user of the software application 225 may provide this information to the input device 1030a. For example, the user interface may include a "location" selection option and/or icon. The user of the interface may tap this icon and then enter a location for the medical equipment. Similarly, the user interface may include an "identification" selection option and/or icon. The user of the interface may tap this icon and then enter identification information for the medical equipment. Location information may include a physical address, a location description, a geolocation and/or an indoor location. Identification information may include a serial number, a model number, and/or another identifiable feature associated with the medical equipment 120.

Figure 10A:
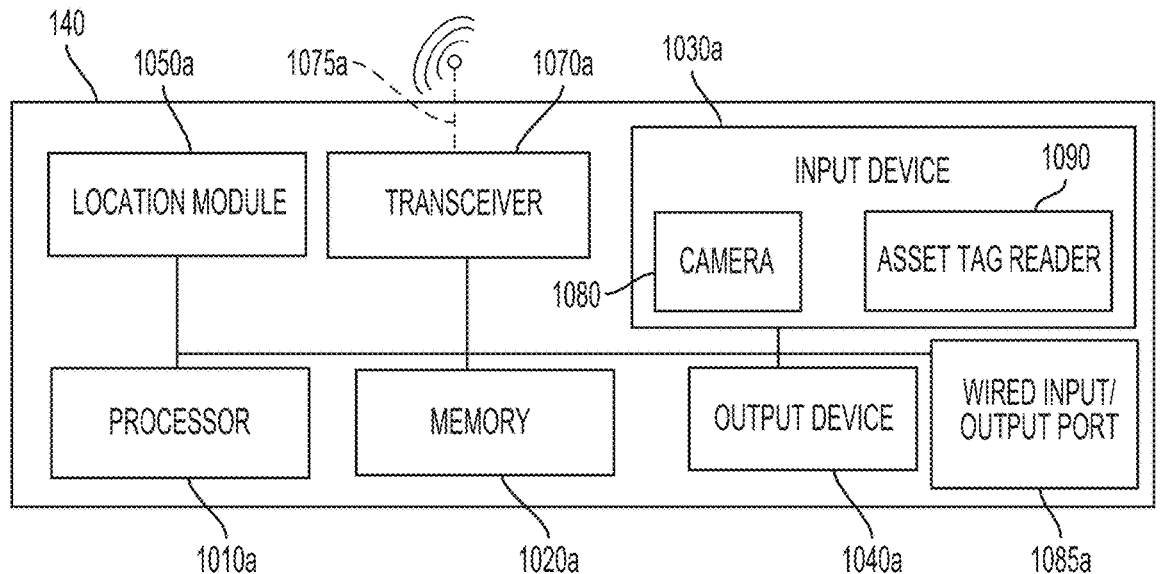
FIG. 10A shows a schematic diagram of an example of computing device components.
Figure 10B:
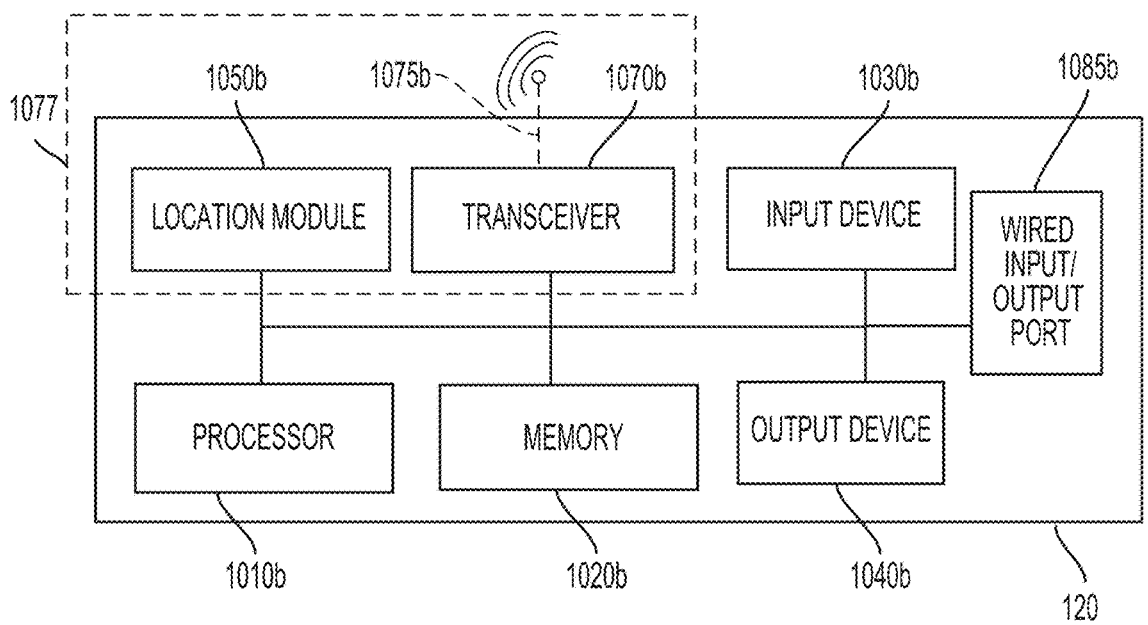
FIG. 10B shows a schematic diagram of an example of medical equipment components.

In addition to, or as an alternative to, capturing inspection information provided to the user interface, the software application 225 may be configured to capture information transmitted by the medical equipment 120. For example, the software application 225 may receive signals transmitted by the medical equipment over a wired and/or wireless connection between the medical equipment 120 and the computing device 140. For a wired connection, the computing device 140 may capture this information via a wired input/output port 1085a (e.g., as shown in FIG. 10A). The medical equipment may include a complimentary wired input/output port 1085b (e.g., as shown in FIG. 10B). For example, the ports 1085a and 1085b may be universal serial bus (USB) ports. For a wireless connection, the computing device 140 may capture this transmitted information via the transceiver 1070a. The transmitted information may include location information, identification information, a media access control (MAC) address, internet protocol (IP) address and/or other network address.

Alternatively, or additionally, the software application 225 may capture medical equipment information via the camera 1080, the asset tag reader 1090, and/or anther input device 1030a of the computing device 140. For example, the medical equipment may include an asset tag (e.g., the barcode 235 and/or the radio frequency identification (RFID) tag 236) compatible with the asset tag reader 1090.

In an implementation, the software application 225 and/or the management system 270 may evaluate and/or compare the location of the medical equipment 120 (e.g., the location obtained from the database 280 and/or determined based on information stored on, entered into, and/or captured by the computing device 140) and the location of the computing device 140 (e.g., as determined by the location module 1050a and/or based on information stored on, entered into and/or captured by the computing device 140) to manage equipment inspections. In turn, the medical equipment management software application may use the location of the computing device 140 and the location of the medical equipment 120 to determine, verify, and/or validate that the inspector 110 is within a predetermined inspection distance from the medical equipment 120. The software application 225 may provide an indication and/or a prompt to the display or other output device of the computing device 140 to notify the inspector 110 that he/she is at or within the predetermined inspection distance (e.g., he/she is at an acceptable distance from the medical equipment 120 to perform the inspection).

For example, the inspection of the medical equipment 120 may include a physical inspection. The physical inspection may include a determination, by the inspector, of at least a portion of the inspection information for the medical equipment 120 and an entry, by the inspector, of that inspection information to a medical equipment management software application installed on the computing device 140. In this case, the predetermined inspection distance between the computing device 140 and the medical equipment 120 may be a physical distance between the inspector and the medical equipment at which the inspector can accurately perform the inspection. Since the inspector 110 and the computing device 140 may be co-located, this predetermined inspection distance may be a physical distance between the computing device 140 and the medical equipment 120. If the physical inspection requires the inspector to view, hear, and/or touch the medical equipment 120, then the predetermined inspection distance may be an inspection distance threshold beyond which the inspector would be unlikely to view, hear, and/or touch the medical equipment 120. As an example, referring again to FIG. 1, the medical equipment 120 may include an equipment status indicator 130 that indicates the operational status of the medical equipment 120. The status indicator 130 may provide a first status indicator that indicates that the medical equipment is in working order and a second status indicator that indicates that the medical equipment is in non-working order. The first and second status indicators may be one or more of a symbol, a color, a word, a picture, etc. In the example of FIG. 1, the first status indicator is a check mark graphic and the second status indicator is an "X" graphic. The status indicator 130 may be a visible indicator on a display (e.g., a graphic, a word, and/or a color), an audible sound from a speaker (e.g., a tone, a sequence of sounds, and/or spoken words), a tactile indicator (e.g., a raised set of bumps), etc. In order to accurately inspect the medical equipment 120, the requisite inspection distance between the inspector 110 and the medical equipment 120 may be a distance at which the inspector can, for example, see, feel, and/or hear the equipment status indicator 130. Thus, the predetermined inspection distance may be a threshold distance beyond which the inspection cannot be accurately performed. For example, if the inspector 110 is further from the medical equipment 120 than the predetermined inspection distance, then the inspector 110 may not be able to view the status indicator 130 with sufficient clarity to ascertain the operational status of the medical equipment 120. As another example, if an inspector is further from a fire extinguisher than the predetermined inspection distance for the fire extinguisher, then the inspector may not be able to manipulate a test button on the fire extinguisher. As a further example, an item of medical equipment may include a low battery alarm and predetermined inspection distance may be a distance within which the inspector can hear the alarm and identify the source of the alarm. In an implementation, the predetermined inspection distance may take into account location constraints for inspection (e.g., line of sight impediments or other viewing constraints).

In another implementation, the physical inspection of the medical equipment 120 may be an inspection based on information contained in signals transmitted via a wired and/or wireless communicative coupling between the medical equipment 120 and the computing device 140. Such a physical inspection may or may not require the inspector to visually, aurally, and/or tactilely inspect the medical equipment 120 but may require the inspector to bring the computing device 140 within a predetermined inspection distance. For example, the predetermined inspection distance may include a signal transmission range or an information capture range (e.g., a range at which the camera 1080 may capture information, such as an image, and/or a range at which the asset tag reader 1090 may capture asset tag information). For the wired connection, the predetermined inspection distance may include a length of the wired connection (e.g., a cable enabled, for example, with a universal serial bus connector) between the computing device 140 and the medical equipment 120. For the wireless connection, for example, the predetermined inspection distance between the computing device 140 and the medical equipment 120 may include an asset tag reader information capture range and/or a radio signal transmission range (e.g., the range for communication via NFC, Bluetooth® Low Energy, Zig-Bee®, Bluetooth®, Wi-Fi®, etc.).

In some implementations, the inspection may include an inspection by the inspector (e.g., the visual, aural and/or tactile inspection) in combination with an inspection based on information transmitted by the medical equipment 120.

In an implementation, the predetermined inspection distance may include a distance between the computing device 140 and the medical equipment 120 that enables a short-range communicative coupling, for example tap-to-connect, and/or other near field communications technologies (e.g., mutual image, motion, pressure and/or sound recognition technologies). For example, the communicative coupling may be a secure wireless communication channel established between devices responsive to a proximity-based interaction between the devices. For example, in an implementation including tap-to-connect enabled devices (e.g., the computing device 140 and the medical equipment 120), a user of the computing device 140 may tap this device on the medical equipment 120 to activate a security-protected communicative coupling. Mutual authentication and a secure communications channel may be established in response to the proximity-based interaction, and the devices can then exchange appropriate information.

Data transfer with such a communication channel may occur in a simple, immediate and transparent fashion (e.g., without entering passwords by the user, setting up networks, connecting cables, and/or pressing a sequence of buttons). The establishment of the communication channel may constitute a handshake process involving the interchange of one or more encrypted identifiers between the two or more devices, and resultant device identity authentication. Rather than requiring the user to potentially spend significant amounts of time in manually configuring the system of each device, or accessing a screen to view and then select from possible device connections, a first device (e.g., the computing device 140) and a second device (e.g., the medical equipment 120) may be preconfigured to communicatively connect (e.g., pair) automatically, by being in close physical proximity to one another and/or with one or more simple actions. The actions may include, for example, tapping of the first device against a tap zone on the second device, an acoustic interaction between the first device and the second device, image recognition of the first device or a portion of the first device by the second device, recognition by the second device of a gesture made by the first device, transmission of an electromagnetic (e.g., electronic, radio frequency, etc.) signal from the first device to the second device via a short-range communication protocol (e.g., Near-Field communications (NFC), radio frequency identification (RFID), Bluetooth®, Bluetooth® Low Energy, ZigBee®, or another short-range communication protocol), or another type of proximity-based interaction. The proximity-based interaction may be a simple, efficient interaction that does not take significant time or attention on the part of the user of the computing device 140. The two devices in contact with each other or positioned within a threshold distance (e.g., less than 100 cm, less than 50 cm, less than 20 cm, less than 15 cm, less than 10 cm, less than 5 cm, less than 2 cm, less than 3 cm, less than 4 cm) of each other. The coupling process may dynamically set parameters of the communication channel and establish a secure, encrypted NFC channel.

The NFC protocol includes a set of communication protocols that enable two electronic devices (e.g., the computing device 140 and the medical equipment 120) to establish communication by bringing them within approximately 4 cm (2 in) of each other. NFC is a set of short-range wireless technologies, typically requiring a separation of 10 cm or less. NFC facilitates the integration of contactless technology into active device platforms, such as mobile phones. NFC is a short-range RFID technology operating at the 13.56 MHz radio frequency (RF) band and is described in the ISO 18092/ECMA 340 and in ISO 21481/ECMA 352 standards. NFC may be specified to be compatible with contactless systems adhering to ISO 14443, ISO 15693 and/or FeliCa. The standards specify both 'passive' and 'active' operation. Passive NFC devices may include tags and/or other transmitters that can send information to other NFC devices without the need for a power source in the passive NFC device. Thus the passive NFC device may not process information sent from another source. The active NFC devices are able to send and receive information and may communicate with other active devices and/or with passive devices. The NFC device may act like a contactless token, interacting with a reader, or act like a reader, powering and interacting with a contactless token. Two NFC devices may also interact with each other in active, or peer-to-peer (P2P) mode, when brought in close proximity. In this active mode, devices take turns to transmit an RF field, e.g. the computing device 140 may turn on its RF field and transmit data to the medical equipment 120, followed by the computing device turning off its field and the medical equipment 120 turning on its field and transmitting data to the computing device 140. While the wireless communications channel may employ a NFC protocol, it should be understood that other communications protocols (e.g., Bluetooth®, Bluetooth® Low Energy, ZigBee®, amongst others) may be employed for the wireless communications.

Various communication paths are shown in FIG. 2A that include wireless and/or wired communication systems and protocols for long-range communications, short-range communications, or combinations thereof. The long-range communications may be communications via the computer network 250 and/or the cellular network 255. For example, the cellular network 255 may include multiple cell sites where each site may have a maximum range of up to approximately one-half mile (1600 meters). In some situations, each site may have a maximum range of up to approximately five miles (8000 meters). In contrast, the short-range communications may be communication ranges of, for example, 4 cm-100 meters. For example, the computing device 140 and the medical equipment 120 may establish near field communications (NFC) when the computing device 140 and the medical equipment 120 are within centimeters or are in contact with one another. In this example, the computing device 140 and the medical equipment 120 may include the hardware and software needed to implement NFC. The use of NFC may enable the establishment of communications over a range of less than or equal to about 4 cm. In another example of short-range communications, the computing device 140 and the medical equipment 120 may use wireless local area network (WLAN) communication technology standards (e.g., IEEE 802.11 based standards) to communicate with one another. The use of WLAN communication technology standards may enable the establishment of communications over a range of less than or equal to about 70 meters. In a further example of short-range communications, the computing device 140 and the medical equipment 120 may use the Bluetooth® wireless technology standard to communicate with one another. The use of Bluetooth® may enable the establishment of short-range communications over a range of less than or equal to about 100 meters. A variant of Bluetooth®, namely Bluetooth® Low Energy (BLE) may enable the establishment of short-range communications over a range of less than or equal to about 50 meters. A device using BLE may consume less power than a device using Bluetooth® or other types of wireless communication systems and protocols. It may be advantageous, therefore, when a computing device's power may be limited (e.g., it operates on a battery) to use BLE.

When the distance between the computing device 140 and the medical equipment 120 is within the range (e.g., touching, ≤4 cm, ≤50 meters, ≤100 m, etc.) of the short-range communication system utilized by the computing device 140 and the medical equipment 120, the medical equipment 120 may discover the computing device 140 and/or the computing device 140 may discover the medical equipment 120. Once discovered, the computing device 140 may provide information to the medical equipment 120, the medical equipment 120 may provide information to the computing device 140, and/or the medical equipment 120 and the computing device 140 may exchange information. In an implementation, the user 110 may enable or disable the short-range communication capabilities of the computing device 140 and/or the medical equipment 120. For example, the user 110 may indicate on the computing device 140 that the software application 225 may perform an action on the computing device 140 when the computing device 140 is within a short-range communication range of the medical equipment 120. When the medical equipment 120 is in proximity to the computing device 140, the medical equipment 120 and/or the computing device 140 may wake up (e.g., transition out of a sleep or reduced power mode) and proceed to recognize each other (e.g., the computing device 140 and the medical equipment 120 may communicate with one another using the wireless short-range communication system).

In an implementation, the medical equipment 120 and/or the computing device 140 may determine their separation distance from one another based on the short-range communication signals. For example, the medical equipment 120 and/or the computing device 140 may determine the separation distance based on received signal strength, transmission power, angle of arrival, bilateration, and/or trilateration. In an implementation, the separation distance determination may involve analysis of beacon signals. In an implementation, the medical equipment 120 and/or the computing device 140 may send the communication signal information to the system 270. The system 270 may determine the separation distance and provide the separation distance to one or more of the medical equipment 120 and the computing device 140.

Once a wireless communicative connection is made between the computing device 140 and the medical equipment 120, even if one or more other devices are located nearby, information may be sent back and forth between the connected devices in a reliable and secure manner (e.g., according to HIPAA standards, 802.11i protocols, etc.) using any suitable type of communication. In some embodiments, to maintain accurate and secure communications, the proximity-based interaction may invoke an authentication protocol, such as the use of encrypted keys, vector initialization, hash encryption, digital certificates, etc., ensuring no drops and/or leakage of data transfer between devices.

The request for connection may include or may be based on an identifier of the first device. The identifier may include a predetermined key or code that indicates to the second device the origin of the first device. Or, the identifier may include data related to the sensed feature(s) that are used for mutual authentication and/or establishing the secure channel.

Authentication of the first device may help to ensure that the device that made the request is the device that is enabled to couple to the medical equipment 120 via the wireless communication channel. Authentication can thus help to prevent unauthorized or unintentional access to the wireless communication channel with the medical equipment 120.

In some examples, both the request by the first device and the authentication of the first device can be performed through a single proximity-based interaction, or by simply bringing the devices within a suitable distance relative to one another. In some examples, the request by the first device and the authentication of the first device are performed by separate proximity-based interactions. In some embodiments, prior to authentication, device addresses, associated user codes, and passwords are pre-configured into memory and/or storage of each device so that upon initiation of the proximity-based interaction between pre-configured devices, the authentication protocol may be triggered for initiating and establishing the secure connection.

The wireless communication channel between the computing device 140 and the medical equipment 120 may be established responsive to a request from a first device (e.g., the computing device 140 or the medical equipment 120) to establish a connection with a second device. For example, the computing device 140 may be the first device and the medical equipment may be the second device. Alternatively, the medical equipment 120 may be the first device and the computing device 140 may be the second device.

In an implementation, the medical equipment 120 may provide (e.g., broadcast, unicast, or multicast) a beacon signal that identifies the medical equipment 120 to the software application 225. The beacon signal may enable the medical equipment 120 and the computing device 140 to locate and recognize one another. Upon receipt of this message, the software application 225 may respond in order to establish a communications channel between the medical equipment 120 and the computing device 140. The medical equipment 120 may provide this message on a schedule (e.g., a power cycling schedule that provides enough power at some regular intervals to the medical equipment 120 for the medical equipment 120 to provide the beacon signal). Alternatively or additionally, the medical equipment 120 may be configured to provide the beacon signal and/or to communicatively couple to the computing device 140 in response to an audible and/or tactile request. For example, the computing device 140 and/or the user 110 may provide an audible wake-up command. In response, the medical equipment 120 may fully and/or partially power-up and communicate with the computing device 140. As another example, the user 110 may tap the medical equipment 120 as a tactile wake-up command.

Once the wireless communication channel has been established, medical equipment information, including, for example, status information, software updates, and/or configuration updates, may be exchanged between the first and second devices.

In an implementation, the software application 225 may evaluate the location of the computing device 140 and provide an indication or prompt to the display of the computing device 140 that notifies the inspector 110 that he/she is at an acceptable distance to request a transmission of inspection information from the medical equipment 120. The medical equipment 120 may transmit the inspection information in response to the request. Additionally, or alternatively, the medical equipment may automatically transmit (e.g., may not require a request for information) the inspection information according to a predetermined transmission schedule or in response to detecting the computing device. As a further possibility, the software application 225 may evaluate the location of the computing device 140 to automatically trigger such a transmission. For example, the computing device 140 may be configured to automatically communicate with the medical equipment 120 (e.g., as initiated by the medical equipment 120 or the mobile device 140) upon the computing device 140 coming within a requisite proximity to the medical equipment 120.

In an implementation, in response to the establishment of a communication link between the medical equipment 120 and the computing device 140, the medical equipment 120 may perform self-test and/or diagnostic functions to determine status information regarding, for example, expiration and/or functional status of components (e.g. electrodes, batteries, etc.) and/or to confirm installation of software updates, etc. In an implementation, the software application 225 may evaluate the location of the medical equipment 120 and/or evaluate the status of a communicative channel with the medical equipment 120 to provide an indication or prompt to the display of the computing device 140 that indicates that the computing device 140 is at an acceptable distance to request performance of the self-test and/or diagnostic functions and/or to receive the status information and/or other information from the medical equipment 120.

As another example, the inspector may select a particular item of medical equipment 120 via the user interface of the computing device 140. Upon selection, the computing device 140 and the medical equipment 120 may establish a communicative connection and the computing device 140 may receive the inspection information from the medical equipment.

The predetermined inspection distance may be a value determined by the software application 225 and/or the management system 270. This distance may be a fixed value or may be an adjustable value. In an implementation, the predetermined inspection distance may be a user configurable value. In an implementation, the predetermined inspection distance may define a geographic area. For example, the area may be an area defined by a radius such as, for example, the predetermined inspection distance. As other examples, the area may be an area defined by one or more physical structures, an area defined according to boundaries on a map, or an area defined by a travel time from a particular reference point. The physical structure may be for example, a hospital, a school, a residential building, an office building, a health club, a store, a facility such as a mall, an airport, a stadium, a portion of a building such as a wing or a floor, etc. In an implementation, the area may be configurable via the software application 225 and/or the management system 270. The configuration of the area may be via a mapping application, a menu driven utility, a list of locations, etc. For example, subscriber to the management system 270 may have permission to configure an area assigned to a respective inspector 110, computing device 140, and/or associated with a particular group of medical equipment. The predetermined inspection distance may be an inspection distance threshold indicative of maximum separation between the computing device 140 and the medical equipment 120 for which entry of inspection information is enabled. The inspection distance threshold may be a same threshold for a group of medical equipment or may be specific to a particular item of medical equipment. Alternatively, this threshold may be specific to a particular item of medical equipment. This threshold may be based on the type of medical equipment and/or the type of status information provided by the medical equipment.

Figure 2B:
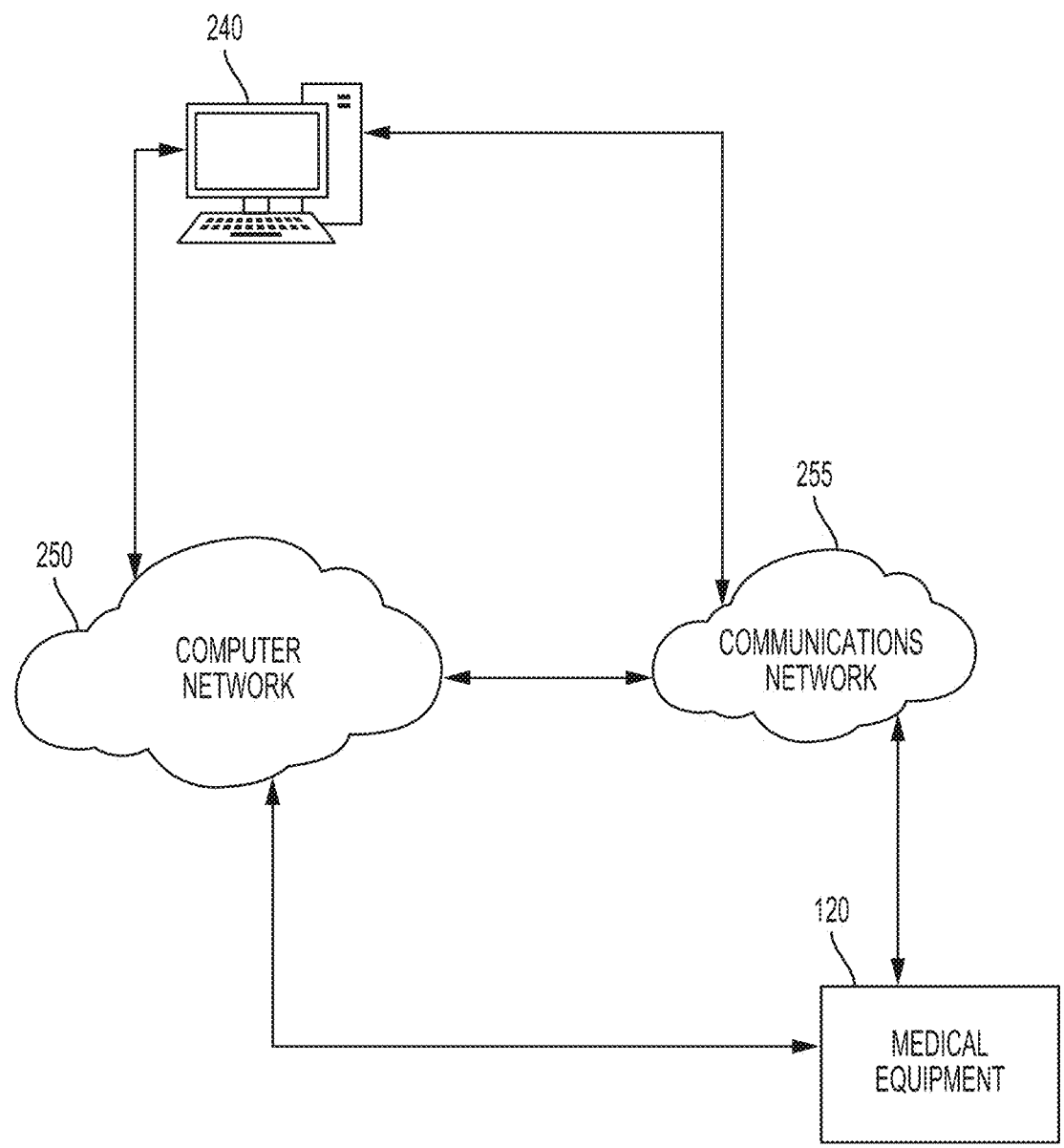
FIG. 2B shows examples of communicative links between the medical equipment and a remote computing device.

Referring to FIG. 2B, examples of communicative links between the medical equipment and a remote computing device are shown. These links may enable a remote inspection of the medical equipment. In an implementation, the medical equipment 120 may initiate and perform self-test and/or diagnostic functions to determine status information regarding, for example, expiration and/or functional status of components (e.g. electrodes, batteries, etc.), to confirm installation of software updates, etc. based on a predetermined and/or programmed schedule. Alternatively, or additionally, the medical equipment 120 may initiate and perform the self-test and/or diagnostic functions in response to a request from the remote computing device 240. Further, the medical equipment 120 may provide status information to the medical equipment management system 270 via the remote computing device 240 and/or may receive new and/or updated software and/or configurations from the medical equipment management system via the remote computing device 240. The remote computing device 240 may include the medical equipment management software application 225 and/or may provide information to one or more mobile devices that include the software application 225.

In an implementation, the software application 225 may update or modify inspection information based on information provided by the remote computing device 240. Further, the software application 225 may provide routing, navigation, and/or location information for remotely inspected medical equipment. For example, if a remote inspection indicated that a particular item of medical equipment or components thereof was expired or malfunctioning, the software application 225 may provide location information for the particular item of medical equipment. As another example, the software application 225 may indicate that components and/or software for a particular item of medical equipment had been changed or updated and may direct an inspector to this equipment for a confirmation of the change or update.

Based on the location of the selected medical equipment and the location of the computing device 140, the software application 225 and/or the management system 270 may enable or disable (e.g., allow or disallow) entry of inspection information for particular medical equipment. For example, the processor 1010a may control the input device 1030a to enable the input of the inspection information and/or other medical equipment information if the distance between the location of the medical equipment and the location of the computing device is within a predetermined distance which may be the predetermined inspection distance. The predetermined distance may also be a distance based on geographic restraints (e.g., authorization for inspections within certain boundaries) and/or other equipment management determinations of an acceptable inspector location. Further, the processor 1010a may control the input device 1030a to disable the input of the medical equipment information if the distance between the location of the medical equipment and the location of the computing device 140 exceeds the predetermined distance.

In order to ascertain the location of the computing device 140, the software application 225 and/or the management system 270 may receive a geolocation for the computing device 140 and/or an indoor location of the computing device 140 from the location module 1050a of the computing device 140. The software application 225 and/or the management system 270 may compare the received location of the computing device 140 with medical equipment location information in the database 280 to determine the proximity of the computing device 140 to the medical equipment. As an additional capability, the software application 225 may provide mapping information and may capture interactive user input based on the mapping information.

In an implementation, the software application 225 may receive the location of the computing device via one or more user inputs to the software application 225. For example, the software application 225 may capture the user-input location if settings of the computing device 140 prevent the software application 225 from accessing the location information for the computing device 140. Additionally, or alternatively, the software application 225 may receive the user-input location if the computing device 140 is disconnected (e.g., offline) from the communications network 255 and/or the computer network 250 and/or if SPS satellite signals and/or radio transmitter signals are unavailable and/or too weak for use in location determination. The software application 225 may provide the location of the computing device 140 to the management system 270 and/or may store the location locally on the computing device 140 (e.g., in the memory 1020a). The software application 225 may store an indication that the location for the computing device 140 is the user-input location. This indication may be available to the account manager. In this manner, the account manager may determine if the location determined from user-input is appropriate for the particular inspector, the particular inspection account and/or the particular item(s) of medical equipment. In an implementation, the software application 225 may restrict user-input of the computing device location to selected inspectors, inspection accounts, items of medical equipment, etc. The user-input location may include one or more of a physical address, a location description, a site description, a name of a building, etc. The physical address may include a street address. The software application 225 may convert the user-input location to a geolocation referenced to global coordinates.

In order to ascertain the location of the medical equipment 120 and evaluate compliance with the predetermined inspection distance, the software application 225 and/or the management system 270 may, for example, obtain a previously registered location from the database 280 (e.g., via the communicative connection to the management system 270 and based on the login information and/or account information for the software application 225). The software application 225 may receive the login information and provide the login information and/or the associated management system account information to the management system 270. In response, the management system 270 may obtain the location information from the database 280 and provide the location information to the software application 225 (e.g., via the computer network 250 and/or or the communications network 255). In one implementation, upon a user of the software application logging into the user's account, one or more processors access the medical equipment information stored in the remote database 280 to identify, based on the location of the computing device 140, what registered medical equipment 120 is within a certain distance of the computing device 140 and transmit that information to the computing device 140. For example, the medical equipment that is identified may be within a predetermined inspection distance, or alternatively located at a particular physical site, etc. As another example, the software application 225 may obtain the medical equipment location from the memory 1020a of the computing device 140. The software application 225 may store medical equipment information locally, for example, in order to maintain operations if the computing device 140 is disconnected (e.g., offline) from the communications network 255 and/or the computer network 250. As a further example, the software application 225 may obtain the medical equipment location from user-input to the software application 225 (e.g., a user-input medical equipment location). The input device 1030a may capture the user-input medical equipment location. The user-input medical equipment location may include one or more of a physical address, a location description, a site description, a name of a building, etc. The physical address may include a street address. For instance, the software application 225 may receive the user-input medical equipment location if the computing device 140 is disconnected (e.g., offline) from the communications network 255 and/or the computer network 250. As an additional example, the software application 225 may obtain the medical equipment location based on the location of the computing device 140. For example, if the computing device 140 is close enough to the medical equipment 120 to capture identification information and/or location information from the medical equipment (e.g., via a wired and/or wireless connection between the medical equipment 120 and the computing device 140 and/or via the camera 1080, via the asset tag reader 1090), then the computing device 140 may be proximate to the medical equipment 120. In this case, the software application 225 may use the location of the computing device 140 as the location of the medical equipment.

In yet a further example, the software application 225 may obtain the medical equipment location via a user-interactive map on a display of the computing device 140. The user-interactive map may include a pin and/or another graphic indicator, at the registered location of the medical equipment 120. The user of the software application 225 may drag and drop the pin and/or the other indicator to update or change the registered location of the medical equipment 120. The location update may enable the software application 225 to operate in the absence of connectivity to the computer network 250 and/or the communications network 255.

In an implementation, the software application 225 and/or the management system 270 may calculate a distance between the medical equipment 120 and the computing device 140. For example, the locations of the medical equipment 120 and the computing device 140 may be geolocations and the distance between the medical equipment 120 and the computing device 140 may be calculated based on the global coordinates of the geolocations. As another example, the locations of the medical equipment 120 and the computing device 140 may be indoor locations. The indoor locations may be associated with coordinates on an indoor map. The distance between the medical equipment 120 and the computing device 140 may be calculated based on the coordinates on the indoor map. As a further example, the locations of the medical equipment 120 and the computing device 140 may be indoor locations referenced to global coordinates or a combination of the indoor location referenced to global coordinates and a geolocation.

In a further implementation, the software application 225 and/or the management system 270 may estimate a distance between the medical equipment 120 and the computing device 140 based on a physical site associated with at least one of the medical equipment 120 and the computing device 140. The physical site may include for example a street address or a site description or name (e.g., parking lot, breakroom, fitness center, lobby, fire truck, police car, ambulance, operating room, office location, library, bank, airport, hospital, store name, etc.). Further, the physical site may include subsets for a site (e.g., one or more offices within an office building, one or more buildings within an office park, one or more areas within an outdoor, outdoor/indoor, or indoor complex, etc.). For example, the locations of the medical equipment 120 and the computing device 140 may both be a physical site. Alternatively, the location of one of the medical equipment 120 or the computing device 140 may be a geolocation or indoor location and the location of the other of the medical equipment 120 or the computing device 140 may be the physical site. The software application 225 and/or the management system 270 may obtain the physical site associated with the medical equipment from the database 280. Alternatively, or additionally, the software application 225 and/or the management system 270 may obtain the physical site associated with the medical equipment from user-input to the software application 225. Further, the software application 225 and/or the management system 270 may obtain the physical site associated with the computing device 140 based on an association between a physical site and the geolocation or indoor location of the computing device 140 and/or the medical equipment 120 and a physical site (e.g., as determined from mapping information).

In an implementation, the medical equipment 120 may initiate a request for inspection and may push the inspection request to the computing device 140. For example, the medical equipment 120 may push the inspection request to the computing device 140 based on the computing device 140 being within the pre-determined inspection distance. The medical equipment 120 may broadcast, multicast, or unicast a beacon signal to locate a computing device 140 within the pre-determined inspection distance. As another example, the medical equipment 120 may push the request to the computing device 140 via an established short-range communication channel. For instance, the short-range communication channel may be a near field communication channel the existence of which indicates that the computing device 140 is proximate to the medical equipment 120.

In an implementation, the server 272 that provides the medical equipment management system 270 and/or the server 282 that provides the medical equipment database may push software and/or configuration updates to the medical equipment 120 via the computing device 140 that provides the software application 225. For example, the computing device 140 may receive the software and/or configuration updates from the server 272 and/or 282 via the communications network 255 (e.g., a cellular communication) and/or the computer network 250 (e.g., a Wi-Fi communication). The computing device 140 may store the software and/or configuration updates locally (e.g., in the memory 1020*a* as shown in FIG. 10A). In an implementation, the server 272 and/or 282 may push the software and/or configuration updates to the computing device 140. The medical equipment management system 270 may instruct the software application 225 to download the updates from the server 272 and/or 282. Alternatively or additionally, the computing device 140 may receive a notification from the server 272 and/or 282 that the software and/or configuration updates are available. In response to the notification, the computing device 140 may request a download of the updates. This request may be automated (e.g., via a configuration of the software application 225) or may be in response to a captured input from the user 110 of the software application 225. In an implementation, the user 210 of the remote computing device 240 may request the updates. In an implementation, the server 272 and/or 282 may require a trusted application (e.g., the software application 225) in order to provide the updates to the computing device 140. In an implementation, the computing device 140 may pull the software and/or configurations updates from the server 272 and/or 282. For example, a start and/or restart of the software application 225 and/or of the computing device 140 may instruct the computing device 140 to pull any available software and/or configuration updates from the server 272 and/or 282 via the medical equipment management system 270.

In an implementation, the computing device 140 may push the locally stored updates to the medical equipment 120 based on a determination that the computing device 140 is proximate to the medical equipment 120. The computing device 140 and the medical equipment 120 may be considered proximate, for example, when the computing device 140 and the medical equipment 120 are at or within a communications range of one another. The communications range may depend on a particular communications protocol and/or technology.

In an implementation, the computing device 140 and medical equipment 120 may be considered proximate, for example, when the computing device 140 and the medical equipment 120 are at or within a particular physical distance from one another. For example, the software application 225 may determine that the computing device 140 is proximate to one or more items of the medical equipment 120 based on a stored location of the medical equipment. In an implementation, the software application 225 may access the medical equipment database 280 to obtain the location of the medical equipment. At the time of determining the proximity of the medical equipment 120, the software application 225 may access the database 280 and/or may access downloaded and locally stored information (e.g., in the memory 1020a as shown in FIG. 10A). Database or local memory access may depend on the network connectivity of the computing device 140 (e.g., to the network 250 and/or 255) at the time of determining the proximity of the medical equipment 120.

In an implementation, the software application 225 may enable the server 272 to stream the software and/or configuration updates to the medical equipment 120. Such streaming may require connectivity of the computing device 140 to one or more of the networks 250 and 255. The software application 225 may enable the communications protocols necessary to communicate with the server 272 and with the medical equipment 120 in order to receive the software and/or configuration updates from the server 272 and/or 282 and pass them along to the medical equipment 120. In the streaming implementation, the computing device 140 may communicate with the medical equipment via a short-range communication technology and/or protocol.

In order for the medical equipment 120 to accept the software and/or configuration updates, the computing device 140 and/or the user 110 may initiate a full and/or partial powering-on of the medical equipment 120. For example, the computing device 140 and/or the user 110 may provide an audible wake-up command. The medical equipment 120 may provide a voice-activated and/or sound-activated response. In response, the medical equipment 120 may fully and/or partially power-up and communicate with the computing device 140. As another example, the user 110 may tap the medical equipment 120 and/or press a button, soft-key and/or other control device as a tactile wake-up command.

In an implementation, the medical equipment 120 may pull software and/or configuration updates from the computing device 140. For example, the medical equipment 120 may initiate a request to the computing device 140 software and/or configuration updates. In an implementation, the medical equipment 120 may provide a broadcast, unicast, or multicast beacon signal. The beacon signal may include the pull request or the medical equipment 120 may provide the pull request in response to a mobile device acknowledgement of the beacon signal. The medical equipment 120 may provide this beacon signal on a schedule. The beacon signal may enable the medical equipment 120 and the computing device 140 to locate and recognize one another. In an implementation, the medical equipment 120 may initiate the request for updates in response to a user initiated trigger. For example, the user 110 may power on the medical equipment 120 and/or activate a hardware and/or software switch or control to trigger the request for updates. In various implementations, the trigger may include one or more of switch actuation, pressing a button, near field communication connection, radio frequency, location recognition, proximity recognition, gestural code, tap recognition, bump recognition, motion-activated, sound, vibration, amongst others. As another example, the user 110 may provide an audible and/or tactile command to wake-up the medical equipment and trigger the request for updates. The medical equipment 120 may provide a voice-activated and/or sound-activated response. The response may be the pull request for updates. In an implementation, the medical equipment 120 may inquire if an update is available and/or may inquire if the computing device 140 will provide the updates at a current date and/or time or at a later date and/or time. For example, the software application 225 may provide user options so that the user 110 may control the data and/or time at which the computing device 140 provides the updates to the medical equipment 120. As another example, the software application 225 may automatically control the date and/or time at which the computing device 140 provides the updates to the medical equipment 120. The software application 225 may also include an option to deny an update in response to a pull request.

Once an exchange or transfer of information (e.g., status, inspection, updates, etc.) is underway between the computing device 140 and the medical equipment 120, the software application 225 may provide a status report. The status report may indicate the progress of the information exchange or transfer (e.g., a numerical and/or graphical indication of a fraction of the total information exchange or transfer that is complete). The status report may indicate that the exchange or transfer is underway without the progress indication. The status report may indicate that the exchange or transfer is complete. The status report may indicate a distance beyond which the short-range communication between the computing device 140 and the medical equipment 120 may cease to support the information exchange or transfer. If the user moves the computing device 140, the status report may warn the user 110 that the location of the computing device 140 is approaching a distance that may no longer support the information exchange or transfer. If the user 110 move the computing device 140 beyond a distance that supports the information exchange or transfer, the software application 225 may provide an error message that indicates that the information exchange or transfer was incomplete. The software application 225 may store this error message locally at the computing device 140 and/or may provide this error message to the medical equipment management system 270. The system 270 may store this error message, for example, in the medical equipment database 280.

Figure 4A:
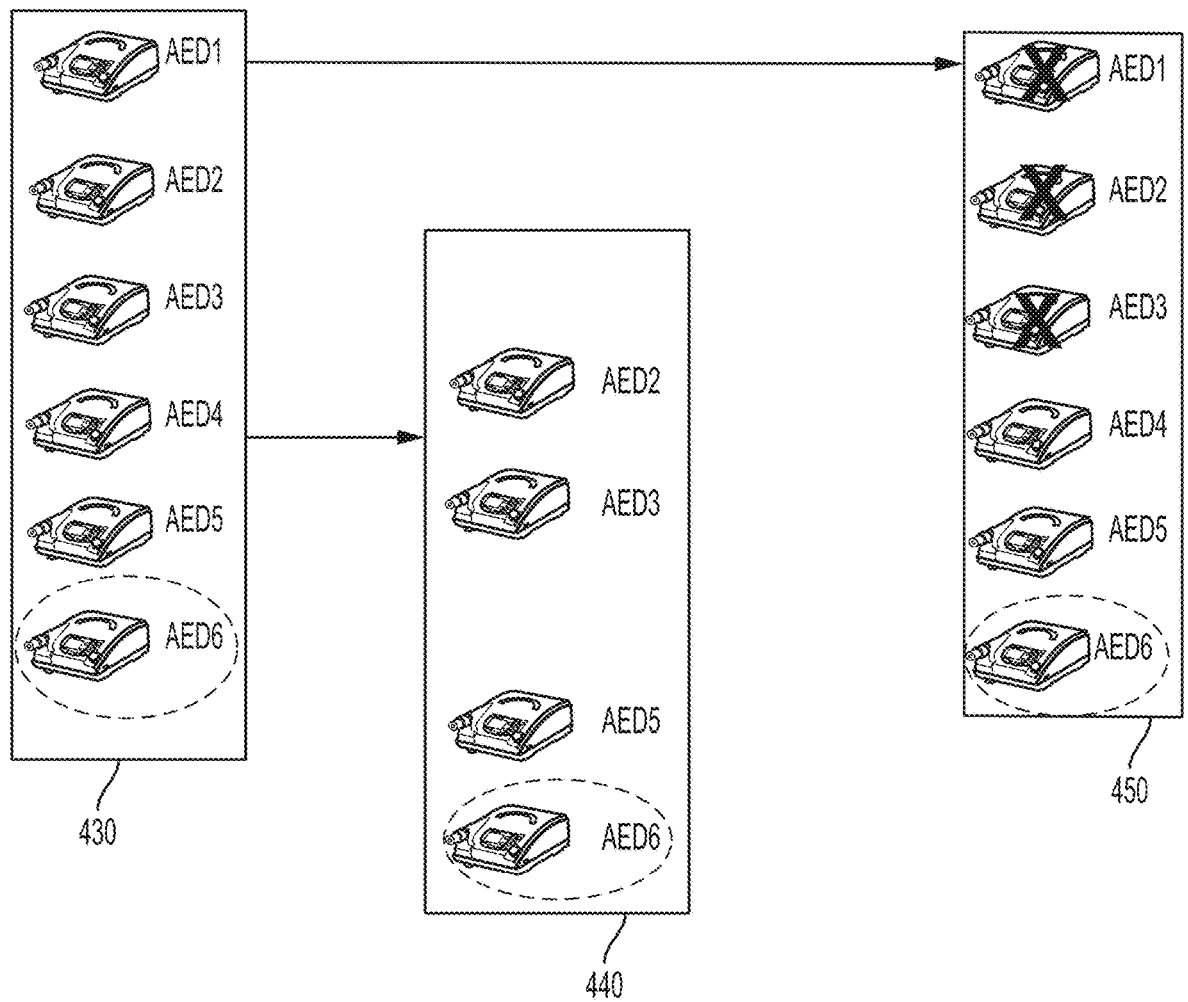
FIGS. 4A and 4B show examples, schematically, of selectively enabled capture of the medical equipment information.
Figure 4B:
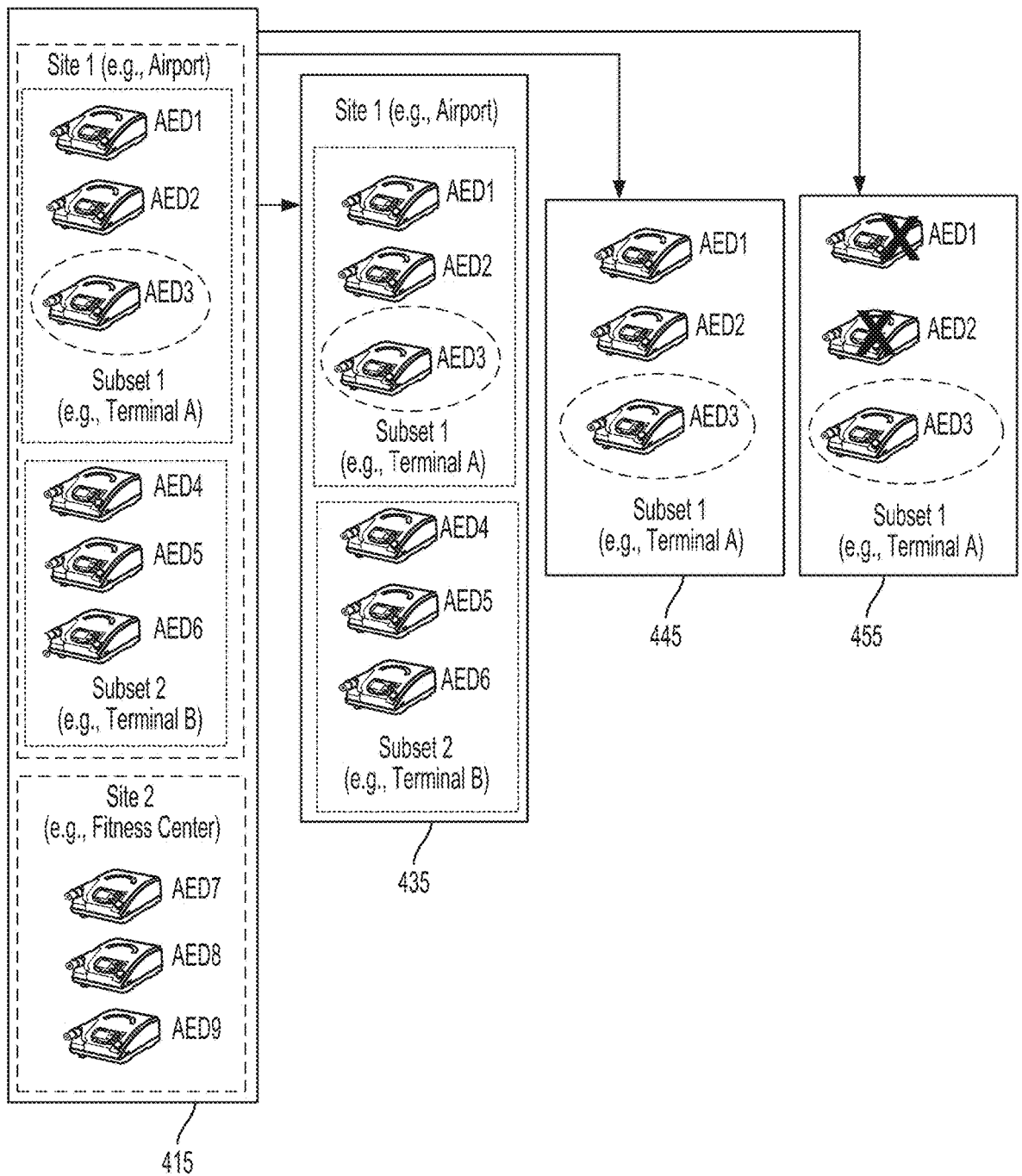

Referring to FIGS. 4A and 4B, examples of selectively enabled capture of the medical equipment inspection information are shown schematically. In an implementation, the software application 225 and/or the medical equipment management system 270 may selectively enable the input of the inspection information based on the location of the computing device 140. In the examples of FIGS. 4A and 4B, the medical equipment is shown as AEDs. However, the AED is an example only and not limiting of the disclosure as other types of medical equipment are within the scope of the disclosure. Additionally, the medical equipment may be all of one type or may be a variety of types of medical equipment. In the examples discussed below with regard to FIGS. 4A and 4B, the software application 225 and/or the management system 270 may selectively enable capture of the medical equipment inspection information based on a distance between the medical equipment 120 and the computing device 140.

In an implementation, the processor 1010*a* may execute instructions of the software application 225 to control the output device 1040*a* to provide a list of medical equipment for which entry of inspection information may be enabled. The list may include all or a portion of the medical equipment associated with the management account and/or the inspection account. The processor 1010*a* may control the output device 1040*a* of the computing device 140 to automatically provide the list in response to the user logging into the software application 225. Alternatively, the processor 1010*a* may receive a user-input request (e.g., input provided to the input device 1030*a* of the computing device 140) for the list and may provide the list in response to the user-input request. As a further alternative, the software application 225 may provide the list in response to a user-input location of the medical equipment 120 and/or the computing device 140. The processor 1010*a* may control the output device 1040*a* to provide a prompt reminding the user to request the list and/or provide the user-input location.

The entry of the inspection information and/or other medical equipment information may be enabled for some or all of the medical equipment on the list based on the location of the computing device 140 and/or based on the location of the computing device 140 relative to a location of the medical equipment 120. For example, the software application 225 may require that the computing device 140 be within the predetermined inspection distance of the medical equipment 120. Further, even if the computing device 140 is within a predetermined inspection distance from a particular item of medical equipment, the software application 225 may selectively enable/disable entry based on privileges associated with the inspection and/or management account information. For example, the inspection account may limit inspections to particular types of medical equipment. As another example, the inspection account may require that inspections be performed at a particular time of day and/or day of the week or at particular time intervals and may disallow non-compliant inspections.

In an implementation, the software application 225 may determine the list of medical equipment locally at the computing device 140. For example, the software application 225 may store medical equipment information in the memory 1020*a*. This information may be previously downloaded from the database 280 and/or may be provided to the computing device 140 by the user and/or via a communicative coupling with the medical equipment 120. Alternatively, or additionally, the management system 270 (e.g., as operated by the server 272) may determine the list and provide the list to the software application 225. The list may be based on one or more lists of medical equipment associated with an inspection account and/or a medical equipment management account. The processor 1010*a* may execute instructions of the software application 225 to control the input device 1030*a* to capture user input indicative of medical equipment selected for inspection.

Medical equipment information for all of the medical equipment associated with the inspection account and/or the medical equipment management account may be available in the database 280 and/or on the computing device 140. The software application 225 may access and receive this information, from the memory 1020*a* and/or from the database 280 via the management system 270. For example, the software application 225 may request this information from the management system 270 and receive the information in response to the request.

As an example, the list 430 of selectable equipment may include all of the medical equipment associated with the user account(s). In this example, the software application 225 may allow the user to select any of the medical equipment associated with the user account for entry of inspection information. For example, on the list 430, all of the AEDs (e.g., AED1-AED6) are shown and AED6 is the selected item of medical equipment from the list for information entry. As another example, the software application 225 and/or the management system may selectively enable selection of medical equipment on the list that is within the predetermined inspection distance from the location of the computing device 140 but disable selection of medical equipment from the provided list that is located further from the location of the computing device 140 than the predetermined inspection distance.

Alternatively, the software application 225, and/or the management system 270, may select a subset of medical equipment associated with the user account(s) as available for entry of inspection information. The list may include the portion of medical equipment in this subset and exclude the remainder of the medical equipment associated with the user account(s). The software application 225 and/or the management system 270 may determine the subset based on the location of the computing device 140 and/or based on a determined distance between the computing device 140 and the medical equipment 120. For example, while the list of medical equipment at 430 includes AED1, AED2, AED3, AED4, AED5, and AED6, the list at 440 only includes the subset of AED2, AED3, AED5, and AED6. AED6 is indicated as the selected AED for inspection (i.e., the selected item of medical equipment from the list for information entry).

As another example, the list 450 of selectable equipment may include all of the medical equipment associated with the user account but may disallow selection of a subset of the medical equipment. In this example, AED1, AED2, and AED3 include an indication (e.g., an "X") that these AEDs are not available for user selection for inspection information entry. AED6 is indicated as the selected AED for inspection. The software application 225 may display or otherwise make AED management information for AED1, AED2, and/or AED3 available to the user of the software application 225 but may not accept input that would alter the database record associated with these AEDs. In other words, the software application 225 may make the medical equipment management information available as read-only information and disable the ability for the user of the software application 225 to edit or change this information and disable the ability for the user of the software application 225 to enter inspection information.

Referring to FIG. 4B, the software application 225 may provide a list with the medical equipment grouped by site and/or grouped by locations within a site. The list may include all of the medical equipment associated with the user account(s). Alternatively, the list may include a portion of the medical equipment associated with one or more sites. In an implementation, the one or more sites may be selected (e.g., by the software application 225 and/or the management system 270) based on the computing device location and the site location. For example, the one or more sites shown in the list 415 of selectable equipment may be sorted based on a distance between each of the one or more sites and the location of the computing device. Further, the provided list may sort and/or order the sites according to proximity to the computing device 140. Additionally, the provided list may sort and/or order the medical equipment within each site based on proximity to the computing device 140. In an implementation, the software application 225 and/or the management system 270 may allow entry of inspection information for a group of medical equipment associated with a site based on a distance between the computing device 140 and that site.

For example, in the list 415, AED1-AED6 are associated with a first site (e.g., site 1) and AED7-AED9 are associated with a second site (e.g., site 2). In this example, site 1 is an airport and site 2 is a fitness center. The AEDs associated with site 1 are further grouped by locations within the site. For example, AED1-AED3 are in subset 1 and are located within the airport at terminal A. AED4-AED6 are in subset 1 and are located within the airport at terminal B. The sites represented in the list 415 may include all of the sites associated with inspection account and/or the management account. In this example, AED3 is the selected item of medical equipment from the list for information entry and/or inspection.

Alternatively, the sites represented in the list 435 may include one or more sites within the predetermined inspection distance from the computing device 140 and exclude one or more sites beyond the predetermined inspection distance from the computing device 140. In this example, sites 1 and 2 are associated with the account. However, the software application 225 and/or the management system 270 may determine that the computing device 140 location is within the predetermined inspection distance only for site 1 (e.g., only for a subset (e.g., one or more) of the sites associated with the account). The software application 225 may provide information to the user interface of the computing device 140 indicating that the computing device 140 is within and/or is proximate to a site (e.g., the airport in the example list 435) that includes one or more items of medical equipment associated with the inspection account and/or the management account. The software application 225 and/or the medical equipment management system 270 may accept inspection information for medical equipment 120 located at the one or more sites that are within the predetermined inspection distance from the computing device 140. In this example, AED3 is the selected item of medical equipment for information entry and/or inspection.

As a further example, the list 445 of selectable equipment may include a subset of locations at a particular site. In this example, the software application 225 and/or the medical equipment management system 270 may allow inspection information entry for medical equipment 120 located Terminal A of the airport and disallow inspection information entry for medical equipment 120 located at Terminal B.

As an additional example, the list 455 may include the subset of locations at the particular site but may disallow selection of a subset of the medical equipment. In this example, AED1 and AED2 include an indication (e.g., an "X") that these AEDs are not available for user selection for inspection information entry. For example, AED1 and AED2 may be located beyond the predetermined inspection distance from the computing device 140. In this example, AED3 is indicated as the selected AED for inspection information entry.

In an additional implementation, the software application 225 and/or the management system 270 may sort or order one or more of the lists (e.g., the lists 430, 440, 450, 415, 435, 445, and 455) of medical equipment available for selection based on proximity to the computing device 140. Further, the software application 225 and/or the management system 270 may automatically select the item of medical equipment on any of the given lists for inspection information entry as opposed to accepting a user selection. This determination may be based on a proximity between the computing device 140 and the medical equipment and/or an establishment of a communicative coupling between the computing device 140 and the medical equipment. For example, the user interface may provide a graphic or textual indication (e.g., a light, an arrow, a change of color, a label, a brightness change, a font and/or graphic size, etc.) of the selected medical equipment.

In an implementation, the software application 225 may provide navigation information and/or medical equipment location information to the user interface. For example, the software application 225 may provide the navigation information automatically to the user interface based on the location of the computing device and the distance between the computing device 140 and the medical equipment 120. The navigation information may be indoor navigation information and/or outdoor navigation information. The navigation information may provide a route and/or routing instructions to navigate between a current location of the computing device 140 and the medical equipment 120 and/or a site that includes the medical equipment 120. The medical equipment location information may include a street address, a location description, a site name, a geolocation, etc. As another example, the software application 225 may provide the navigation information and/or the medical equipment location information to the user interface in response to a request from the user of the software application 225. The request may include a request for locations of medical equipment associated with the inspection account and/or management account and within a particular distance of and/or area around the computing device 140. For example, the particular distance may be the predetermined inspection distance, a user configurable distance, or a distance based on an estimated travel time for the user. As another example, the area around the computing device may be a predetermined inspection territory for the user. As a further example, the area may be within a site (e.g., inside a building or within a commercial or residential complex) proximate to the computing device 140.

In an implementation, the software application 225 may allow entry of the inspection information regardless of the distance between the computing device 140 and the medical equipment 120. The software application 225 may provide the entered inspection information to the management system 270. The management system 270 may store the entered inspection information in the database 280. The inspection information may include the location of the computing device 140 at the time of inspection data entry. Further, the management system 270 may determine whether or not the computing device 140 was within the predetermined inspection distance from the medical equipment. If the computing device 140 was located beyond the predetermined inspection distance and/or outside of an area defined by the predetermined inspection distance, then the management system 270 may include an indication in the medical equipment inspection information stored in the database 280 (e.g., a flag or other marker) that the computing device 140 was beyond the predetermined inspection distance and/or outside of an area defined by the predetermined inspection distance when the computing device 140 captured the inspection information. A manager of the medical equipment may evaluate the inspection information and the location of the computing device 140 at the time of the inspection from a maintenance log retrieved from the database 280.

In a further implementation, the software application 225 may store the inspection information locally (e.g., in the memory 1020*a*). The locally stored inspection information may include the location of the computing device 140 at the time of inspection data entry. Further, the software application 225 may determine whether or not the computing device 140 was within the predetermined inspection distance from the medical equipment. If the computing device 140 was located beyond the predetermined inspection distance and/or outside of an area defined by the predetermined inspection distance, then the software application 225 may include an indication in the medical equipment inspection information stored in the memory 1020a (e.g., a flag or other marker) that the computing device 140 was beyond the predetermined inspection distance and/or outside of an area defined by the predetermined inspection distance when the computing device 140 captured the inspection information. The software application 225 may store the inspection information locally, for example, if the computing device 140 is disconnected (e.g., offline) from the communications network 255 and/or the computer network 250. The software application 225 may upload the inspection information to the management system 270. The upload may occur automatically when a communications link between the computing device 140 and the management system 270 is established or re-established. Alternatively, or additionally, the software application 225 may require an input request from the user to upload the inspection information.

Referring to FIG. 5, in an implementation, the software application 225 may provide one or more of the above described lists as visible information on a display and/or audible information from a speaker (e.g., visible and/or audible information provided by the output device 1040a). The lists may be provided in a text format and/or as mapping information. For example, as shown in FIG. 5, the list of medical equipment may be a text list. As another example, the mapping information may include one or more icons, pins, and/or other graphic indicators. The one or more icons, pins, and/or other graphic indicators may indicate the location(s) of one or more items of medical equipment. Additionally or alternatively, the one or more icons, pins, and/or other graphic indicators may indicate the locations of one or more of responders, inspectors, patients, landmarks, etc.

Figure 7:
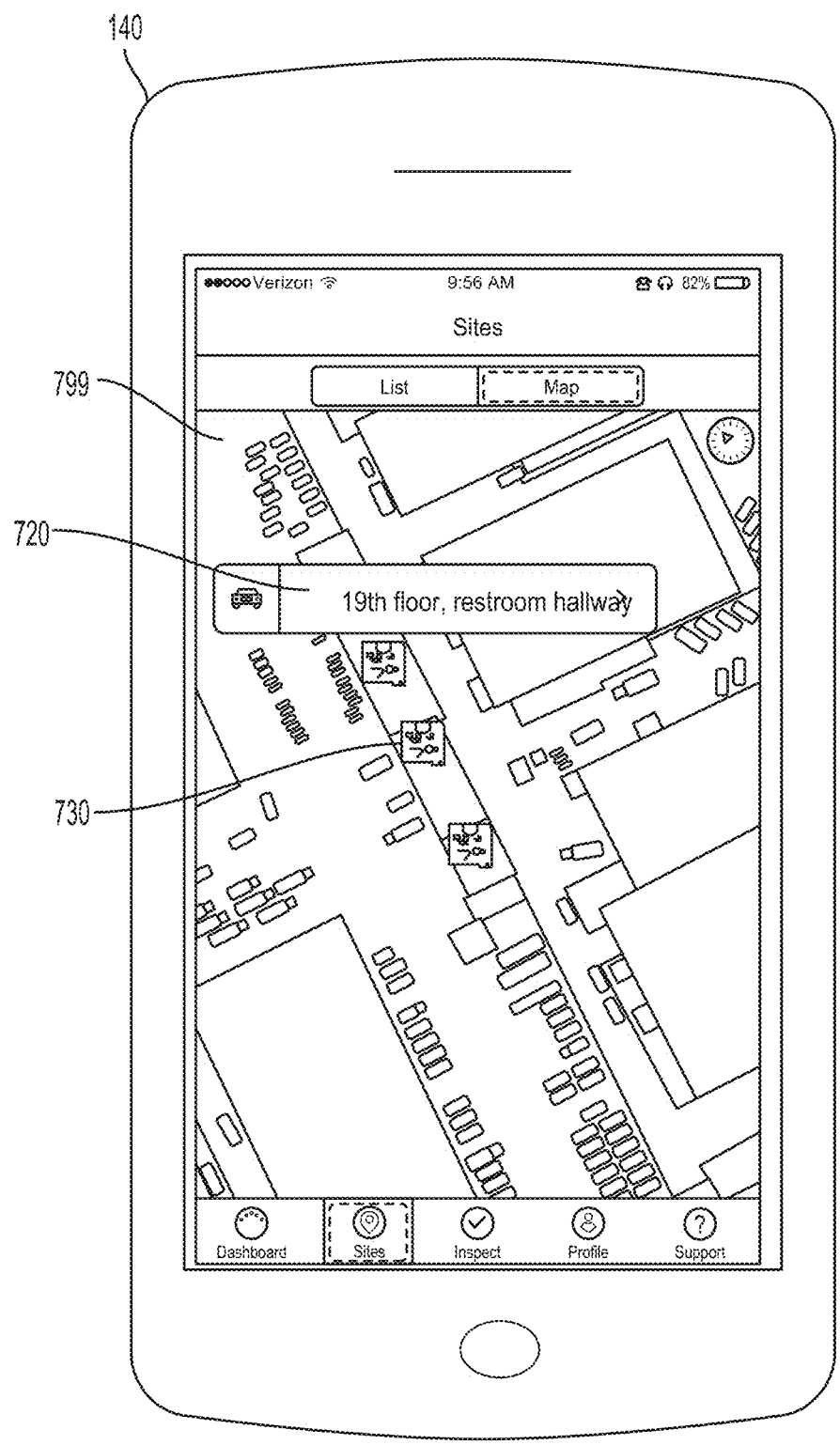

Referring to FIGS. 6 and 7, alternatively, or additionally, the list of medical equipment may be provided as mapping information. FIG. 6 shows a low-resolution map 699 and FIG. 7 shows a high-resolution map 799. The displayed mapping information may include icons (e.g., the icon 730). The icons may indicate the location(s) of one or more items of medical equipment. Additionally or alternatively, the icons may indicate locations of one or more of responders, inspectors, patients, landmarks, etc.

In various implementations, the medical equipment 120 may be transported medical equipment. For example, an AED may be stored in a mobile storage location rather than a stationary storage location and/or may be transported from a first stationary or mobile storage location to a second stationary or mobile storage location. A wall mounted cabinet is an example of a stationary storage location and a compartment in a vehicle (e.g., an ambulance, a fire truck, a police car, a tow truck, etc.) is an example of a mobile storage location. The medical equipment 120 associated with the mobile storage location and/or the transported medical equipment may be routinely inspected at different locations. Further, the medical equipment 120 may be associated with a registered storage location based on the ownership of the medical equipment 120 but may not be inspected at that location. For example, the registered storage location for an AED may be a fire station. However, a fireperson may put the AED in the firetruck and inspect the AED at a location remote from the fire station. As another example, the transported medical equipment may be a Narcan® kit stored in a police car. The policeperson may inspect the kit periodically but at various geographic locations based on the movement of the police car. As a further example, equipment and/or medications on a hospital crash cart may be moved around a hospital routinely and, therefore, the inspection location might change within the hospital.

In such implementations, the software application 225 may allow a medical equipment location update for transported medical equipment. The software application 225 may store the location update in the database 280 and/or in the memory 1020a of the computing device 140. In an implementation, during the registration process, the management system 270 and/or the software application 225 may designate specific equipment as transported equipment and enable location updates for the equipment designated as transported. In conjunction with the update, the software application 225 may generate an alert that the current location of the computing device 140 is further from the registered location of the medical equipment 120 than a predetermined inspection distance limit (e.g., a radius of an area centered approximately at the registered location of the medical equipment 120). The software application 225 may request the location update in response to or in conjunction with the alert.

For transported medical equipment, the software application may obtain the location information for transported medical equipment based on the location of the computing device and/or may receive a user-input medical equipment. The software application 225 may update a registered location in the database 280 based on the user-input and/or the location of the computing device.

In an implementation, the software application 225 may display a user-interactive map to capture a location of the transported medical equipment and/or to update the registered location in the database 280. The software application may obtain the medical equipment location for the transported medical equipment based on user input to the user-interactive map. The map may include a pin, or other indicator, at the registered location of the medical equipment 120 and/or at a previous location of the medical equipment 120. The user may drag and drop the pin to update the location of the medical equipment 120. Alternatively or additionally, the software application 225 may accept a textual input from the user indicating the location of the medical equipment 120. The user-interactive map may include the current location of the computing device 140.

In an implementation, the management system 270 and/or the software application 225 may register a primary location for the medical equipment 120 along with one or more secondary locations. The software application 225 may display or otherwise provide the primary location and the one or more secondary locations for selection by the inspector. The software application 225 may compare the location of the computing device 140 to the selected location (e.g., the primary location or one of the one or more secondary locations) to determine if the computing device 140 is proximate to the medical equipment 120.

Figure 8:
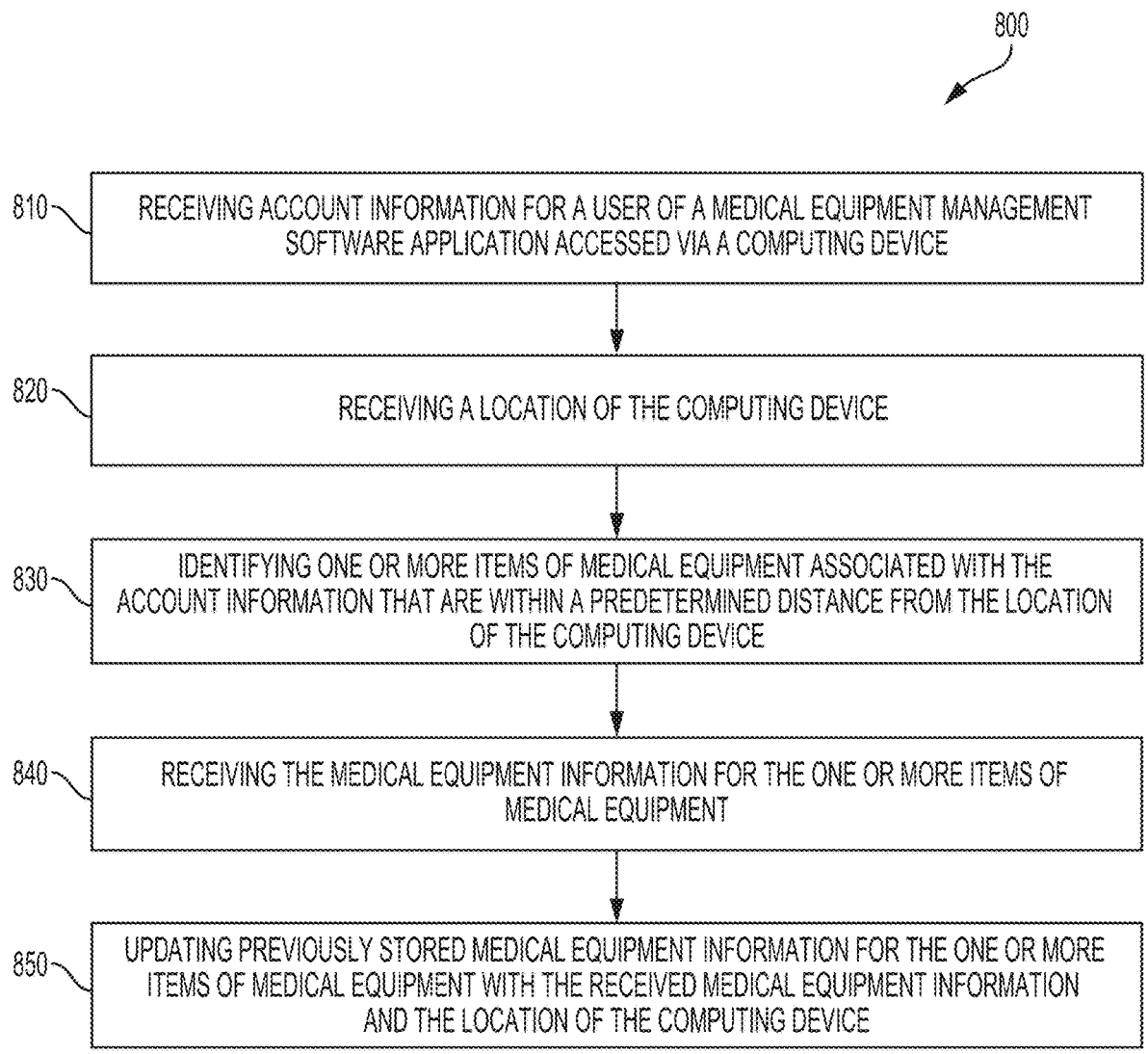
FIG. 8 shows a block diagram of a method for managing medical equipment.

Referring to FIG. 8, a computer-implemented method of verifying medical equipment inspection is shown. The method 800 is, however, an example only and not limiting. The method 800 can be altered, e.g., by having stages added, removed, rearranged, combined, and/or performed concurrently.

At stage 810, the method 800 includes receiving account information for a user of a medical equipment management software application accessed via a computing device. For example, the processor 1010*a* may control the input device 1030*a* of the computing device 140 to capture login information for a user of the software application 225. The login information may be associated with account information for the inspection account and/or the management system account. In an implementation, the software application 225 may be installed on the computing device 140. In a further implementation, the software application 225 may be a computer network based application (e.g., a web-based application). The user may provide the login information to the input device 1030*a*. The login information may include, for example, but not limited to, a user name, a password, a security code, a hardware identification code, and/or a biometric input. The software application 225 may provide the login information to the management system 270 via the computer network 250 and/or the communications network 255. The management system 270 and/or the software application 225 may associate the login information with a management system account and/or an inspection account. One or more items of medical equipment may be associated with the management system account and/or the inspection account. In an implementation, the software application 225 may access medical equipment information in the database 280 via the management system account and/or the inspection account. Alternatively, the software application 225 may access medical equipment information stored on the computing device 140 (e.g., in the memory 1020*a*).

At stage 820, the method 800 includes receiving a location of the computing device. The software application 225 may receive and/or request the location of the computing device 140 at the time of entry and/or receipt of the inspection information.

For example, the software application 225 may receive the location of the computing device from the location module 1050*a*. The mobile device settings may grant permission for the installed software application 225 to access the location information determined by the location module 1050*a*. The determined location may be the SPS-based location and may be a geolocation. As described above, in an implementation, the location of the computing device 140 may be an indoor location referenced to the indoor mapping information for the structure (e.g., the structure 205) in which the computing device 140 is located. In an implementation, the location module 1050*a* may provide the indoor position of the computing device 140 to the software application 225. In a further implementation, the location module 1050*a* may convert the indoor position to a geolocation referenced to global coordinates and then provide the geolocation to the software application 225.

In an implementation, the input device 1030*a* may capture a user-input location for the computing device and provide the user-input location to the software application 225. For example, the software application 225 may capture the user-input computing device location if settings of the computing device 140 prevent the software application 225 from accessing the location information for the computing device 140. Additionally, or alternatively, the software application 225 may receive the user-input location if the computing device 140 is disconnected (e.g., offline) from the communications network 255 and/or the computer network 250 and/or if SPS satellite signals and/or radio transmitter signals are unavailable and/or too weak for use in location determination. The software application 225 may provide the location of the computing device 140 to the management system 270 and/or may store the location locally on the computing device 140 (e.g., in the memory 1020*a*). The software application 225 may store an indication that the location for the computing device 140 is the user-input location. This indication may be available to the account manager. In this manner, the account manager may determine if the computing device location determined from user-input is appropriate for the particular inspector, the particular inspection account and/or the particular item(s) of medical equipment. In an implementation, the software application 225 may restrict user-input of the computing device location to selected inspectors, inspection accounts, items of medical equipment, etc. The user-input computing device location may include one or more of a physical address, a location description, a site description, a name of a building, etc. The physical address may include a street address. The software application 225 may convert the user-input location to a geolocation referenced to global coordinates.

At stage 830, the method 800 includes identifying at least one item of medical equipment associated with the account information. In an implementation, the software application 225 may identify one or more items of medical equipment based on the distances between the computing device 140 and the medical equipment associated with the account information. For example, the software application 225 may identify one or more items of medical equipment 120 that are within a predetermined inspection distance from the computing device 140. The software application 225 may evaluate these distances locally (e.g., at the computing device 140), for example, in order to maintain operations if the computing device 140 is disconnected (e.g., offline) from the communications network 255 and/or the computer network 250. Alternatively, or additionally, the medical equipment management system 270 may evaluate these distances (e.g., at the server 272) and provide a set of identified medical equipment to the software application 225. In an implementation, the software application 225 may obtain location(s) of the medical equipment associated with the account information. For example, these location(s) may include pre-registered location information and/or self-reported location information stored in the database 280 or in the memory 1020*a*.

In an implementation, the medical equipment location(s) may be user-input locations (e.g., locations of the medical equipment provided to the software application 225 by a user of the software application 225). For example, the software application 225 may provide a user-interactive map and the user of the software application 225 may provide the user-input location for the medical equipment 120 via the user-interactive map. As a further example, the location of the medical equipment 120 may be determined from the location of the computing device 140. The user-input location for the medical equipment and/or the location of the medical equipment determined from the location of the computing device 140 may be used for routinely transported medical equipment that has a variable inspection location. Further, the user-input location may be used when the computing device 140 is off-line (e.g., disconnected from the communications network 255). The medical equipment management software application may store an indication that the location for the medical equipment 120 is the user-input location. This indication may be available to the account manager. In this manner, the account manager may determine if the medical equipment location determined from user-input is appropriate for the particular item of medical equipment. In an implementation, the software application 225 may restrict user-input of the medical equipment location to selected items of medical equipment (e.g., restrict user-input to routinely transported medical equipment).

In an implementation, identifying the one or more items of medical equipment may include selectively enabling input of medical equipment information, including inspection information, for the medical equipment. The processor 1010b may selectively enable input by allowing or disallowing entry of the input information and/or receipt of input information by the software application 225. As described with regard to FIGS. 4A and 4B, the selective enablement of entry and/or receipt of the input information may be based on the predetermined inspection distance and the relative distance of the computing device 140 from the medical equipment 120. Further, the software application 225 may provide one or more lists of medical equipment available for inspection. The list(s) may include all or a subset of the medical equipment associated with the account information. Providing the lists may include providing the lists in a text format and/or as mapping information. The software application 225 and/or the management system 270 may determine which medical equipment is included in the lists. The processor 1010a may provide the one or more lists in response to receiving a request, via user-input captured by the computing device 140, for the one or more lists. For example, the processor 1010a may execute instructions of the software application 225 to control the input device 1030a to provide the list(s) and to selectively enable and selectively disable entry and/or receipt of the medical equipment information.

At stage 840, the method 800 includes receiving the medical equipment information for the one or more items of medical equipment. The one or more selected items of medical equipment may be selected for inspection and for entry of inspection information and/or other medical equipment information to the software application 225 and/or the database 280. For example, the computing device 140 receives the medical equipment information from the medical equipment 120. In an implementation, the medical equipment information may include information provided as user-input to an inspection user interface provided at the computing device. Alternatively, or additionally, the medical equipment information may be information provided via signals transmitted from the medical equipment 120 to the computing device 140 and/or via information captured from the medical equipment (e.g., via a camera image, asset tag, RFID tag, etc.). The medical equipment information may also be obtained by the computing device 140 from the medical equipment 120 via a tap-to-connect or other near field communication technology and/or secure near field communication technology.

At stage 850, the method 800 includes updating previously stored medical equipment information for the one or more items of medical equipment with the received medical equipment information and the location of the computing device. For example, the software application 225 may send the inspection information to a server (e.g., the database 280 via the management system 270) via the computer network 250 and/or the communications network 255. As another example, the software application 225 may store the medical equipment inspection information locally at the computing device 140 (e.g., in the memory 1020a). Storing the inspection information may include replacing and/or updating any previously stored inspection information. The stored inspection information may include the location of the computing device as determined at the time of entry and/or receipt of the inspection information. In an implementation, the stored inspection information may include an indication as to whether or not the computing device 140 was within the predetermined inspection distance of the medical equipment 120.

Figure 9:
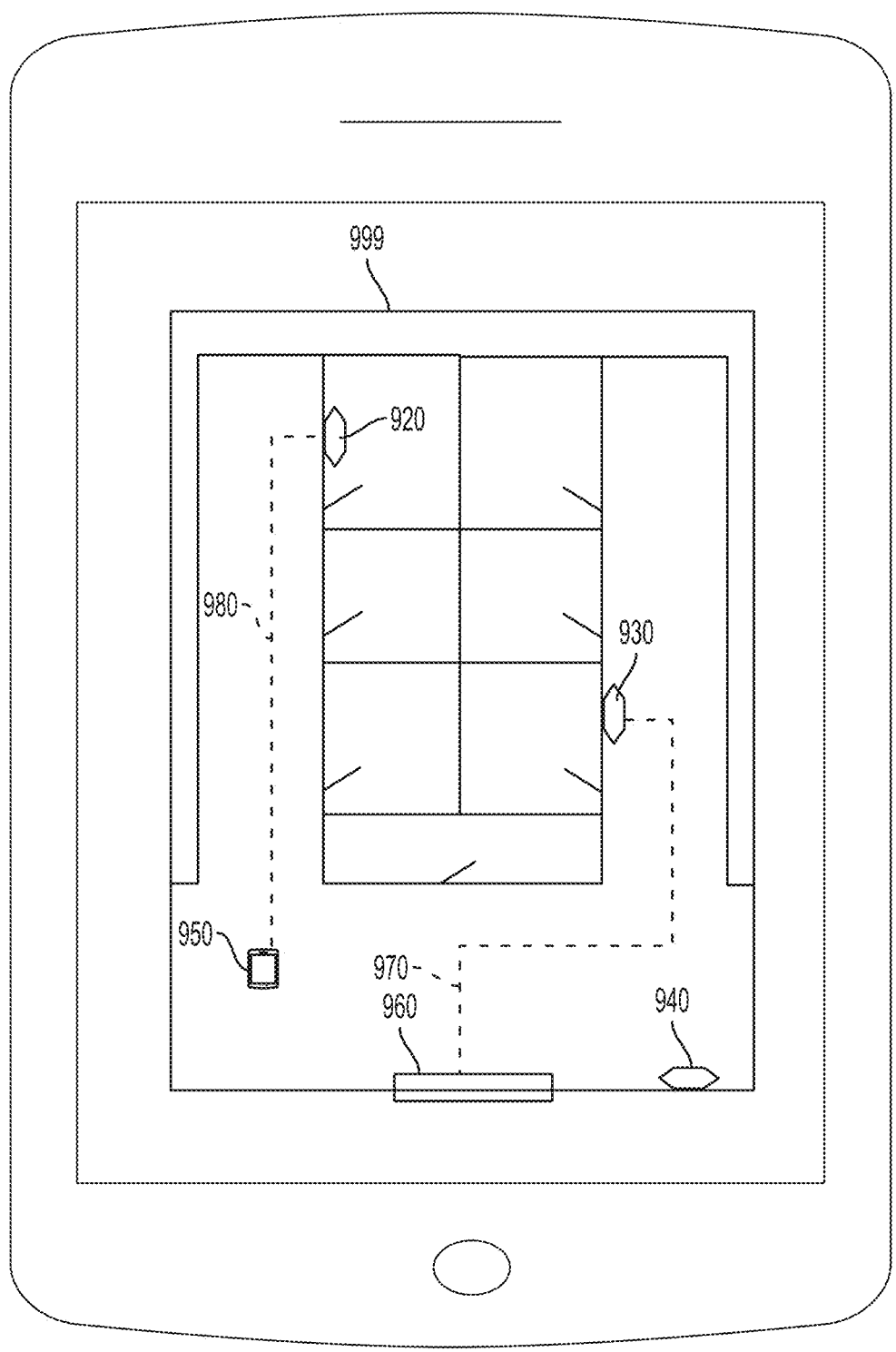
FIG. 9 shows an example of indoor mapping information for medical equipment inspection.

Referring to FIG. 9, an example of indoor mapping information for medical equipment inspection is shown. For example, as described above, the location module 1050a of the computing device 140 may obtain the digital electronic map 999 for an indoor facility in which medical equipment is located at medical equipment locations 920, 930, and 940. In implementation, the digital electronic map may display user-selectable icons. The user-selectable icons may indicate the location(s) of one or more items of medical equipment. Additionally or alternatively, the icons may indicate locations of one or more of responders, inspectors, patients, landmarks, etc. In response to a user selection of a particular icon, the software application 225 may provide navigation information on the digital electronic map of the indoor facility. In various implementations, the navigation information may be mapping information, text information (e.g., a list of navigation instructions), visual information, and/or audible information. In an implementation, the indoor navigation information may be predetermined information providing a previously determined route 970 between the medical equipment location 930 and an indoor location such as, for example, a main door 960. Alternatively, or additionally, the indoor navigation information may be real-time information providing a route between a current location of the computing device 140 and the medical equipment 120. For example, the location module 1050a may provide navigation instructions on the digital electronic map indicative of a navigable route 980 between a current location 950 of the computing device 140 and the medical equipment location 920. The navigation information may guide the user of the software application 225 between the current location 950 of the computing device 140 and the medical equipment location 920 based on interior and/or exterior features (e.g., doorways, hallways, elevators, stairwells, etc.) of the indoor facility 205. In an implementation, the indoor mapping information may include three dimensional location information indicative of medical equipment locations on various floors or levels of an indoor facility. The navigation information may guide the user along one floor and/or between floors to the medical equipment locations.

Referring to FIG. 10A, a schematic diagram of an example of computing device components is shown. For example, the computing device 140 may include the processor 1010a, the memory 1020a, the input device 1030a, the output device 1040a, the location module 1050a, the transceiver 1070a, and the wired input/output port 1085a. The remote computing device 240 may also include one or more of the components shown in FIG. 10A. The components 1010a, 1020a, 1030a, 1040a, 1050a, 1070a, and 1085a are communicatively coupled (directly and/or indirectly) to each other for bi-directional communication. Although shown as separate entities in FIG. 10A, two or more of the components 1010a, 1020a, 1030a, 1040a, 1050a, 1070a, and 1085a may be combined into one or more discrete components and/or may be part of the processor 1010a. The processor 1010a and the memory 1020a may include and/or be coupled to associated circuitry in order to perform the functions described herein. A quantity of each component shown in FIG. 10A is an example only and other quantities of each, or any, component could be used.

Referring to FIG. 10B, a schematic diagram of an example of medical equipment components is shown. For example, the medical equipment 120 may include the processor 1010b, the memory 1020b, the input device 1030b, the output device 1040b, the location module 1050b, the transceiver 1070b, and the wired input/output port 1085b. The components 1010b, 1020b, 1030b, 1040b, 1050b, 1070b, and 1085b are communicatively coupled (directly and/or indirectly) to each other for bi-directional communication. Although shown as separate entities in FIG. 10B, two or more of the components 1010b, 1020b, 1030b, 1040b, 1050b, 1070b, and 1085b may be combined into one or more discrete components and/or may be part of the processor 1010b. The processor 1010b and the memory 1020b may include and/or be coupled to associated circuitry in order to perform the functions described herein. A quantity of each component shown in FIG. 10B is an example only and other quantities of each, or any, component could be used.

The processors 1010a and 1010b are each one or more physical processors (e.g., an integrated circuit configured to execute operations on the computing device 140, the remote computing device 240, or the medical equipment 120 as specified by software and/or firmware). Each of the processors 1010a, 1010b may be an intelligent hardware device, e.g., a central processing unit (CPU), one or more microprocessors, a controller or microcontroller, an application specific integrated circuit (ASIC), digital signal processor (DSP), or other programmable logic device, a state machine, discrete gate or transistor logic, discrete hardware components, or any combination thereof designed to perform the functions described herein and operable to carry out instructions on the computing device 140, the remote computing device 240, or the medical equipment 120. Each of the processors 1010a, 1010b may utilize various architectures including but not limited to a complex instruction set computer (CISC) processor, a reduced instruction set computer (RISC) processor, or a minimal instruction set computer (MISC). In various implementations, each of the processors 1010a, 1010b may be a single-threaded or a multi-threaded processor. Each of the processors 1010a, 1010b may be one or more processors and may be implemented as a combination of computing devices (e.g., a combination of DSP and a microprocessor, a plurality of microprocessors, one or more microprocessors in conjunction with a DSP core, or any other such configuration). Each of the processors 1010a, 1010b may include multiple separate physical entities that may be distributed in the computing device 140, the remote computing device 240, or in the medical equipment 120. Each of the processors 1010a, 1010b is configured to execute processor-readable, processor-executable software code containing one or more instructions or code for controlling the processor 1010a, 1010b to perform the functions as described herein.

The processors 1010a, 1010b are operably coupled, respectively, to the memory 1020a, 1020b. The memory 1020a, 1020b refers generally to any type of computer storage medium, including but not limited to RAM, ROM, FLASH, disc drives, fuse devices, and portable storage media, such as Universal Serial Bus (USB) flash drives, etc. The USB flash drives can store operating systems and other applications. The USB flash drives can include input/output components, such as a wireless transmitter and/or USB connector that can be inserted into a USB port of another computing device. The memory 1020a, 1020b may be long term, short term, or other memory associated with the computing device 140, the remote computing device 240, or the medical equipment 120 and is not to be limited to any particular type of memory or number of memories, or type of media upon which memory is stored. The memory 1020a, 1020b includes a non-transitory processor-readable storage medium (or media) that stores the processor-readable, processor-executable software code.

The input devices 1030a, 1030b may include one or more of a keyboard, a microphone, and a mouse, joystick, trackball, or other pointing device. The processors 1010a and 1010b may, respectively, control the input devices 1030a and 1030b to capture user input. The input device 1030a may further include the camera 1080 and/or the asset tag reader 1090. For example, the asset tag reader 1090 may include an RFID tag reader and/or a barcode scanner.

The output devices 1040a, 1040b may be a one or more of a display, a speaker, and a haptic device. The display may provide a graphical user interface (GUI). The display may be, for example, but not limited to, a liquid crystal display (LCD) and/or a light emitting diode (LED) display. The processors 1010a and 1010b may control, respectively, the output devices 1040a and 1040b to provide one or more of visible information, audible information, haptic information, numerical information, textual information, and graphical information.

In an implementation the input device 1030a and the output device 1040a and/or the input device 1030b and the output device 1040b may be combined as an input/output device capable of capturing user input. For example, the input/output device may be a touchscreen. The wired input/output port 1085a and the wired input/output port 1085b are data and/or communication ports. For example, these ports may be universal serial bus (USB) ports.

The location module 1050a is illustrated separately from the processor 1010a for clarity but may be part of processor 1010a or may be implemented in the processor 1010a based on instructions in software stored in memory 1020a and implemented by processor 1010a. Similarly, the location module 1050b is illustrated separately from the processor 1010b for clarity but may be part of processor 1010b or may be implemented in the processor 1010b based on instructions in software stored in memory 1020b and implemented by processor 1010b. The location modules 1050a, 1050b can, but need not necessarily, include and/or be incorporated into, for example, one or more microprocessors, embedded processors, controllers, application specific integrated circuits (ASICs), digital signal processors (DSPs), etc. The location module 1050a is configured to determine a location of the computing device 140 and the location module 1050b is configured to determine a location of the medical equipment 120.

In an implementation, the location modules 1050a, 1050b may determine locations based on signals from satellite positioning system (SPS) satellites 290 and/or terrestrial radio transmitters (e.g., outdoor radio transmitters 296 and/or indoor radio transmitters 295). The SPS satellites 290 include suitable logic, circuitry, and code to generate and send radio-frequency (RF) SPS signals that may be received at the computing device 140 and/or the medical equipment 120 for use in determining a satellite positioning system based location of the computing device 140 and/or the medical equipment 120. The SPS may include such systems as the Global Positioning System (GPS), Galileo, Glonass, Compass, Quasi-Zenith Satellite System (QZSS) over Japan, Indian Regional Navigational Satellite System (IRNSS) over India, Beidou over China, etc., and/or various augmentation systems (e.g., a Satellite Based Augmentation System (SBAS)) that may be associated with or otherwise enabled for use with one or more global and/or regional navigation satellite systems. As used herein, an SPS may include any combination of one or more global and/or regional navigation satellite systems and/or augmentation systems, and SPS signals may include SPS, SPS-like, and/or other signals associated with such one or more SPS. The terrestrial radio transmitters may include, for example, but not limited to, Wi-Fi®/WLAN access points, Worldwide Interoperability for Microwave Access (WiMAX) nodes, femtocells, communications network base stations and other cellular wireless nodes, a Bluetooth® or other similarly short-ranged wireless node, combinations thereof, and so forth. The indoor radio transmitters 295 may be located internal to the structure 205, external to the structure 205, or on a border of the structure 205 (e.g., partially interior and partially exterior).

In an implementation, the SPS-based location may be a geo-location for the computing device 140 and/or the medical equipment 120. The geolocation may include a two-dimensional location in a global coordinate system (e.g., a latitude and longitude or other earth centered coordinates). The geolocation may further include an elevation (e.g., a three-dimensional location in a global coordinate system). The elevation may be a SPS-based elevation and/or may be an elevation determined based on an indicator of elevation such as barometric pressure.

In an implementation, the location modules 1050a and/or 1050b may determine an indoor location for the computing device 140 and/or the medical equipment 120. Satellite positioning systems (SPS), such as, for example, global positioning systems (GPS) have enabled location determination for computing devices in outdoor environments. However, satellite signals may not always be reliably received and/or acquired in an indoor environment. Therefore, location determination techniques other than SPS-based positioning may be employed to enable indoor position estimation and related navigation services. For example, the location modules 1050a, 1050b may determine the indoor location by measuring ranges to three or more terrestrial radio transmitters including, for example, the radio transmitters 295 and/or 296. In an implementation, the location information may include indoor mapping information that includes indoor locations of medical equipment. In an implementation, the location module 1050b may transmit the location of the medical equipment to the management system 270, the registration system 260, and/or the computing device 140. In this manner, the medical equipment 120 may self-report its location.

The location of the radio transmitter 295 may be a predetermined location relative to indoor mapping information for the structure 205. The location of the radio transmitter 295 and the indoor mapping information for the structure 205 may be stored in a positioning database, for example, at one or more positioning servers. The location modules 1050a and/or 1050b may access the indoor location of the radio transmitter 295 and/or the indoor mapping information via the communications network 255 and/or the computer network 250. The location modules 1050a and/or 1050b may determine measured ranges to the three or more terrestrial radio transmitters, for example, by obtaining a media access control (MAC) address from signals received from such radio transmitters and measuring one or more characteristics of signals received from such radio transmitters such as, for example, a signal strength (e.g., a received signal strength indication (RSSI)) and/or a propagation time (e.g., a round-trip time (RTT)) for signals exchanged with various radio transmitters. The positioning database may identify the indoor location of a particular radio transmitter based on, for example, the MAC address.

The indoor mapping information may include a digital electronic map that includes navigation and routing information and/or location information for indoor features such as doors, hallways, entry ways, walls, etc., points of interest such as bathrooms, conference room names, stores, offices, etc. The indoor features may further include medical equipment locations. Such a digital electronic map may be stored at the positioning server to be accessible by the location module 1050a, 1050b through selection of an Internet-based universal resource locator (URL), for example. In an implementation, the processor 1010a and/or 1010b may control the output device 1040a and/or 1040b to display the digital electronic map. The location module 1050a, 1050b may determine the indoor location of the computing device 140 or the medical equipment 120 relative to the indoor mapping information. In an implementation, the location module 1050a, 1050b may convert the indoor location to a geolocation based on a correlation between the indoor locations and earth coordinates.

The transceivers 1070a, 1070b can send and receive wireless signals via the antennas 1075a, 1075b over one or more wireless networks, for example, the communications network 255 in FIG. 2A. Although shown as single transceivers and antennas in FIGS. 10A and 10B, the transceiver 1070a and/or 1070b and the antenna 1075a and/or 1075b may include multiple transceivers and antennas, for example, to support multiple communication standards such as Wi-Fi®, Code Division Multiple Access (CDMA), Wideband CDMA (WCDMA), Long Term Evolution (LTE), Bluetooth, etc. The transceivers 1070a, 1070b may also be configured to receive SPS signals (e.g., from the SPS satellites 290 in FIG. 2A) used to determine location information. The transceivers 1070a, 1070b may be further configured to enable the computing device 140 and/or the medical equipment 120 to communicate and exchange information, either directly or indirectly with other communications network entities, including but not limited to, other computing devices and/or other medical equipment.

In an implementation, one or more of the location module 1050b, the transceiver 1070b, and the antenna 1075b may be components of a communications device 1077 electronically coupled to the medical equipment 120. The communications device 1077 may be a retrofit or peripheral device (e.g., a dongle) that enables an item of medical equipment 120 to communicatively couple to the computing device 140 and/or to one or more of the networks 250 and 255. For example, the communications device 1077 may electronically couple to the medical equipment 120 via a USB port, a telephone jack, and/or another data port and/or another communications port of the medical equipment 120. In an implementation, the communications device 1077 may electronically couple to the medical equipment 120 via the wired input/output port 1085b. The communications device 1077 may incorporate a connector plug or may include a wire or cable that connects the communications device 1077 to a connector plug configured to electronically couple to the medical equipment 120.

The servers 262, 272, and/or 282 may include or contribute to a cloud storage system. The cloud storage system may reside on one or more servers in a cloud server network. The one or more servers may be communicatively coupled in order to provide cloud computing and cloud storage services to the computing device 140 and/or the remote computing device 240 via the communications network 255 and/or the computer network 250. Cloud computing allows a user of the computing devices 140 and/or 240 to perform computing tasks where data, applications, and even complete virtualized computing systems are accessed via the communications network 255 and/or the computer network 250. The network of servers and connections used to provide the cloud computing service is generally referred to as "the cloud." Cloud storage provides an abstraction for physical storage devices. Cloud storage generally involves delivering data storage as a service, often billed on a usage basis. That is, cloud storage allows users to store and access data files somewhere in "the cloud," without knowing the details of where files are stored or having to manage the physical storage devices. In the cloud storage system, capacity can be available on demand and files can be made available on a global basis.

The software application 225, the management system 270, the registration system 260 and the database 280 described herein can be implemented in digital electronic circuitry, or in computer hardware, firmware, software, or in combinations of them. Firmware and/or software can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device.

A computer program, including the software application 225, is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, 5PROM, and flash memory devices; magnetic disks such as internal hard disks and removable disks; magneto-optical disks; and CD-ROM and DVD-ROM disks.

The computing devices described herein may include, or be operatively coupled to communicate with, one or more mass storage devices for storing data files; such devices include magnetic disks, such as internal hard disks and removable disks; magneto-optical disks; and optical disks.

The terms "machine-readable medium," "computer-readable medium," and "processor-readable medium" as used herein, refer to any medium that participates in providing data that causes a machine to operate in a specific fashion. Using a computer system, various processor-readable media (e.g., a computer program product) might be involved in providing instructions/code to processor(s) for execution and/or might be used to store and/or carry such instructions/code (e.g., as signals).

In many implementations, a processor-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of processor-readable media may be involved in carrying one or more sequences of one or more instructions to one or more processors for execution. Merely by way of example, the instructions may initially be carried on a flash device, a device including persistent memory, and/or a magnetic disk and/or optical disc of a remote computer. A remote computer might load the instructions into its dynamic memory and send the instructions as signals over a transmission medium to be received and/or executed by a computer system.

The computing devices may be part of a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet. The computer system can include clients and servers. A client and server are generally remote from each other and typically interact through a network, such as the described one. The relationship of client and server arises by virtue of computer programs running on the respective computers and having a client-server relationship to each other.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Information and signals may be represented using any of a variety of different technologies and techniques. For example, data, instructions, commands, information, signals, and symbols that may be referenced throughout the above description may be represented by voltages, currents, electromagnetic waves, magnetic fields or particles, optical fields or particles, or any combination thereof.

The methods, systems, and devices discussed above are examples. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory processor-readable medium such as a storage medium. Processors may perform the described tasks.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Components, functional or otherwise, shown in the figures and/or discussed herein as being connected or communicating with each other are communicatively coupled. That is, they may be directly or indirectly connected to enable communication between them. Features implementing functions may be physically located at various locations, including being distributed such that portions of functions are implemented at different physical locations.

As used herein, including in the claims, "and" as used in a list of items prefaced by "at least one of" indicates a disjunctive list such that, for example, a list of "at least one of A, B, and C" means A or B or C or AB or AC or BC or ABC, or combinations with more than one feature (e.g., 1, 1B, A2C, etc.). As used herein, including in the claims, unless otherwise stated, a statement that a function or operation is "based on" an item or condition means that the function or operation is based on the stated item or condition and may be based on one or more items and/or conditions in addition to the stated item or condition.

Having described several example configurations, various modifications, alternative constructions, and equivalents may be used without departing from the disclosure. For example, the above elements may be components of a larger system, wherein other rules may take precedence over or otherwise modify the application of the invention. Also, a number of operations may be undertaken before, during, or after the above elements are considered. Also, technology evolves and, thus, many of the elements are examples and do not bound the scope of the disclosure or claims. Accordingly, the above description does not bound the scope of the claims. Further, more than one invention may be disclosed.

What is claimed is:

1. A system for managing medical equipment, the system comprising:
    a computing device comprising a first memory, an inspection user interface configured to capture one or more user inputs, and one or more first processors, wherein the one or more first processors are configured to:
        receive information that identifies an account associated with a user of the computing device, wherein the information is provided via the one or more user inputs to the inspection user interface,
        present, via the inspection user interface, identification information for at least one item of medical equipment that is associated with the account,
        present, via the inspection user interface, a list of a plurality of components that are included with the at least one item of medical equipment,
        after receiving the information that identifies the account, receive current status information for one or more of the plurality of components, and
        send, to one or more servers, the current status information for the at least one item of medical equipment; and
    the one or more servers comprising:
        a second memory including a database having stored therein previously stored status information for the at least one item of medical equipment,
        a communication component configured to receive the current status information for the at least one item of medical equipment, and
        one or more second processors configured to determine access privileges associated with the account, wherein:
            management access privileges allow the user of the computing device to add information characterizing a new item of medical equipment to the database and update the previously stored status information in the database after receiving the current status information; and
            inspection access privileges allow the user of the computing device to update the previously stored status information in the database after receiving the current status information, but prevent the user from adding information characterizing the new item of medical equipment to the database.

2. The system of claim 1, wherein the at least one item of medical equipment comprises one or more of public safety equipment, emergency equipment, or hospital equipment.

3. The system of claim 1, wherein the at least one item of medical equipment comprises an external defibrillator.

4. The system of claim 1, wherein the at least one item of medical equipment comprises one or more of a naloxone hydrochloride kit, a first aid kit, or tourniquet equipment.

5. The system of claim 1, wherein:
    the one or more first processors are further configured to receive, from the one or more servers, identification information for the at least one item of medical equipment; and
    the identification information is provided based on an inspection distance, evaluated at the one or more servers, between the computing device and the at least one item of medical equipment.

6. The system of claim 1, wherein the one or more first processors are further configured to:
    receive, from the one or more servers, a location of the at least one item of medical equipment; and
    present, via the inspection user interface, the location.

7. The system of claim 1, wherein the one or more first processors are further configured to send, to the one or more servers, current location information for the at least one item of medical equipment.

8. The system of claim 1, wherein:
    updating the previously stored status information in the database includes storing an inspection information entry in the database; and
    the inspection information entry comprises a timestamp associated with an inspection of the at least one item of medical equipment, location information for the at least one item of medical equipment, and the current status information.

9. The system of claim 8, wherein the inspection information entry further comprises a location of the computing device during the inspection of the at least one item of medical equipment.

10. A computer-implemented method for managing medical equipment, the method comprising:

receiving, from a computing device, information that identifies an account associated with a user of the computing device;

determining access privileges associated with the account, the access privileges defining permissions for a database having stored therein status information for at least one item of medical equipment, wherein:

management access privileges allow the user of the computing device to add information characterizing a new item of medical equipment to the database and modify the status information for the at least one item of medical equipment, and inspection access privileges allow the user of the computing device to modify the status information for the at least one item of medical equipment, but prevent the user from adding information characterizing the new item of medical equipment to the database;

receiving, from the computing device, inspection information provided by the user associated with the account; and updating the database based on the received inspection information and in accordance with the determined access privileges associated with the account.

11. The computer-implemented method of claim 10, further comprising sending, to the computing device, a notification that a component of the at least one item of medial equipment is due for replacement or servicing.

12. The computer-implemented method of claim 10, further comprising sending, to the computing device, an expiration date for a component of the at least one item of medical equipment.

13. The computer-implemented method of claim 10, further comprising sending, to the computing device, the status information for the at least one item of medical equipment.

14. The computer-implemented method of claim 10, wherein the received inspection information characterizes results of an inspection of the at least one item of medical equipment.

15. The computer-implemented method of claim 10, wherein the at least one item of medical equipment is a first aid kit.

16. The computer-implemented method of claim 15, wherein the first aid kid includes at least one consumable component.

17. The computer-implemented method of claim 15, wherein the status information includes inventory information for at least one of a plurality of components that are included in the first aid kit.

18. The computer-implemented method of claim 15, wherein the status information includes an expiration date for at least one of a plurality of components that are included in the first aid kit.

19. The computer-implemented method of claim 10, wherein the at least one item of medical equipment includes a processor, a memory, and an input/output device.

20. The computer-implemented method of claim 19, wherein the status information comprises battery information for the at least one item of medical equipment.

21. The computer-implemented method of claim 19, wherein the status information includes at least one of software information or configuration information for the at least one item of medical equipment.

22. The computer-implemented method of claim 19, further comprising sending, to the computing device, a notification that at least one of a software update or a configuration update is available for the at least one item of medical equipment.

23. The computer-implemented method of claim 22, further comprising sending, to the computing device, the at least one of the software update or the configuration update.

24. The computer-implemented method of claim 10, further comprising sending, to the computing device, an equipment list that includes a plurality of items of medical equipment associated with the account.

25. The computer-implemented method of claim 10, further comprising receiving, from the computing device, a location of the computing device, wherein updating the database includes storing the location of the computing device in the database.

26. The computer-implemented method of claim 10, further comprising:

receiving, from the computing device, a location of the computing device; and sending, to the computing device, identification information for one or more items of medical equipment based on a distance between the computing device and each of the one or more items of medical equipment.

27. The computer-implemented method of claim 10, further comprising receiving, from the computing device, a location of the at least one item of medical equipment, wherein updating the database includes storing the location of the at least one item of medical equipment in the database.

28. The computer-implemented method of claim 10, wherein the at least one item of medical equipment comprises one or more of an external defibrillator, an automated external defibrillator, a patient monitor, ventilation equipment, drug delivery equipment, a physiological sensor, a fire extinguisher, an oxygen tank, a naloxone hydrochloride kit, a first aid kit, or tourniquet equipment.

* * * * *